US011946068B2

(12) United States Patent
Bhumiratana et al.

(10) Patent No.: US 11,946,068 B2
(45) Date of Patent: Apr. 2, 2024

(54) SYSTEM AND METHOD FOR SEEDING AND CULTURING

(71) Applicant: EPIBONE, INC., Brooklyn, NY (US)

(72) Inventors: Sarindr Bhumiratana, Long Island City, NY (US); Keith Yeager, Springfield, NJ (US)

(73) Assignee: EpiBone, Inc., Jersey City, NJ (US)

(*) Notice: Subject to any disclaimer, the term of this patent is extended or adjusted under 35 U.S.C. 154(b) by 180 days.

(21) Appl. No.: 17/174,983

(22) Filed: Feb. 12, 2021

(65) Prior Publication Data

US 2021/0163882 A1 Jun. 3, 2021

Related U.S. Application Data

(63) Continuation of application No. 16/603,082, filed as application No. PCT/US2018/026730 on Apr. 9, 2018, now Pat. No. 10,961,501.

(Continued)

(51) Int. Cl.
*C12N 5/00* (2006.01)
*C12M 1/00* (2006.01)
(Continued)

(52) U.S. Cl.
CPC .......... *C12N 5/0068* (2013.01); *C12M 23/20* (2013.01); *C12M 25/14* (2013.01); *C12M 33/00* (2013.01)

(58) Field of Classification Search
CPC ..... C12N 5/0068; C12M 23/20; C12M 25/14; C12M 33/00; C12M 21/08; C12M 29/06;
(Continued)

(56) References Cited

U.S. PATENT DOCUMENTS 6,030,358 A 2/2000 Odland
6,197,575 B1 3/2001 Griffith et al.
(Continued)

FOREIGN PATENT DOCUMENTS

CN 1427888 A 7/2003
CN 102296029 A 12/2011
(Continued)

OTHER PUBLICATIONS

Bornes et al., Bio Protoc. Dec. 20, 2015; 5(24) (Year: 2015).*
(Continued)

*Primary Examiner* — Samuel P Siefke
*Assistant Examiner* — Henry H Nguyen
(74) *Attorney, Agent, or Firm* — Troutman Pepper Hamilton Sanders LLP

(57) ABSTRACT

A system for seeding therapeutic active ingredients (TAIs) onto a porous scaffold includes a first chamber for accommodating the scaffold, a TAI storage device for storing TAIs, at least one second chamber for storing TAI media, and a gas inlet for receiving gas from a compressed source. A flow circuit is coupled to the first chamber, the TAI storage device, the second chamber and the gas inlet for delivering the TAIs, the TAI media and the gas to the scaffold. A pump pumps at least one of the TAIs, the TAI media and the gas in the flow circuit. The system also includes a processor that regulates the delivery of the TAIs, the TAI media and the gas to the scaffold via a plurality of valves.

16 Claims, 17 Drawing Sheets

Related U.S. Application Data

(60) Provisional application No. 62/483,031, filed on Apr. 7, 2017.

(51) Int. Cl.
  *C12M 1/12* (2006.01)
  *C12M 1/26* (2006.01)

(58) Field of Classification Search
  CPC ...... C12M 29/12; C12M 29/20; C12M 29/26; C12M 41/48; C12M 1/10
  See application file for complete search history.

(56) References Cited

U.S. PATENT DOCUMENTS

| | | |
|---|---|---|
| 6,294,041 B1 | 9/2001 | Boyce et al. |
| 6,372,257 B1 | 4/2002 | Marchosky |
| 6,544,788 B2 | 4/2003 | Singh |
| 6,632,651 B1 | 10/2003 | Nevo et al. |
| 7,195,394 B2 | 3/2007 | Singh |
| 7,629,167 B2 | 12/2009 | Hodge et al. |
| 7,635,586 B2 | 12/2009 | West |
| 7,738,682 B2 | 6/2010 | Banes et al. |
| 7,819,934 B2 | 10/2010 | Galliher et al. |
| 8,298,054 B2 | 10/2012 | Hodge et al. |
| 8,328,876 B2 | 12/2012 | Behnam et al. |
| 8,367,410 B2 | 2/2013 | Radisic et al. |
| 8,381,780 B2 | 2/2013 | Fisher et al. |
| 8,435,306 B2 | 5/2013 | Evans et al. |
| 8,468,871 B2 | 6/2013 | Potyrailo et al. |
| 8,492,135 B2 | 7/2013 | Porter et al. |
| 8,608,801 B2 | 12/2013 | Hung et al. |
| 8,722,075 B2 | 5/2014 | Shimp et al. |
| 8,865,199 B2 | 10/2014 | Coleman et al. |
| 8,906,362 B2 | 12/2014 | Ferguson et al. |
| 9,163,212 B2 | 10/2015 | McKay |
| 9,597,359 B2 | 3/2017 | Mao et al. |
| 9,775,931 B2 | 10/2017 | Francis et al. |
| 9,938,502 B2 | 4/2018 | Zhang et al. |
| 9,987,394 B2 | 6/2018 | Meretzki |
| 10,479,977 B2 | 11/2019 | Wang et al. |
| 10,736,991 B2 | 8/2020 | Badylak et al. |
| 10,864,234 B2 | 12/2020 | Tuan |
| 10,874,766 B2 | 12/2020 | Cashman et al. |
| 2001/0021529 A1 | 9/2001 | Takagi |
| 2002/0059049 A1 | 5/2002 | Bradbury et al. |
| 2002/0110905 A1 | 8/2002 | Barbera-Guillem et al. |
| 2002/0171178 A1 | 11/2002 | Dean et al. |
| 2003/0006534 A1 | 1/2003 | Taboas et al. |
| 2003/0161816 A1 | 8/2003 | Fraser et al. |
| 2004/0091459 A1 | 5/2004 | Nimni |
| 2004/0219659 A1 | 11/2004 | Altman et al. |
| 2004/0241835 A1 | 12/2004 | Hutmacher et al. |
| 2005/0002910 A1 | 1/2005 | Wolfinbarger et al. |
| 2006/0024822 A1 | 2/2006 | Chang et al. |
| 2006/0105011 A1 | 5/2006 | Sun et al. |
| 2006/0141623 A1 | 6/2006 | Smith et al. |
| 2007/0233272 A1 | 10/2007 | Boyce et al. |
| 2007/0276501 A1 | 11/2007 | Betz et al. |
| 2008/0033572 A1 | 2/2008 | D'Antonio et al. |
| 2008/0113426 A1 | 5/2008 | Smith et al. |
| 2009/0035856 A1 | 2/2009 | Galliher et al. |
| 2009/0233362 A1 | 9/2009 | Chen et al. |
| 2009/0298173 A1 | 12/2009 | Ueda et al. |
| 2010/0128961 A1 | 5/2010 | Kalusche |
| 2011/0136225 A1 | 6/2011 | Vunjak-Novakovic et al. |
| 2011/0151551 A1 | 6/2011 | Yi et al. |
| 2011/0151552 A1 | 6/2011 | Jiang et al. |
| 2011/0171732 A1 | 7/2011 | Mandoll et al. |
| 2011/0189764 A1* | 8/2011 | Starbard ............ C12M 23/28 435/307.1 |
| 2011/0202142 A1 | 8/2011 | Mao et al. |
| 2011/0212500 A1 | 9/2011 | Boronyak et al. |
| 2012/0028234 A1 | 2/2012 | Guertin et al. |
| 2012/0035742 A1 | 2/2012 | Vunjak-Novakovic et al. |
| 2012/0089238 A1 | 4/2012 | Kang et al. |
| 2012/0122220 A1 | 5/2012 | Merchav et al. |
| 2012/0206155 A1 | 8/2012 | Wang et al. |
| 2013/0017131 A1 | 1/2013 | Galliher et al. |
| 2013/0089925 A1 | 4/2013 | Damren et al. |
| 2013/0196438 A1* | 8/2013 | Chun ............ A61L 27/3826 435/395 |
| 2013/0274929 A1 | 10/2013 | Hodge et al. |
| 2014/0106403 A1 | 4/2014 | Guertin et al. |
| 2015/0018968 A1 | 1/2015 | Sun et al. |
| 2017/0145361 A1* | 5/2017 | Bergmann ............ C12M 23/24 |
| 2017/0227525 A1 | 8/2017 | Griffith et al. |
| 2017/0290665 A1 | 10/2017 | Vunjak-Novakovic et al. |
| 2020/0078411 A1 | 3/2020 | Gimble et al. |

FOREIGN PATENT DOCUMENTS

| | | |
|---|---|---|
| CN | 102304476 A | 1/2012 |
| CN | 102803471 A | 11/2012 |
| EP | 1359214 | 11/2003 |
| JP | 2001-238663 A | 9/2001 |
| JP | 2011-160797 A | 8/2011 |
| WO | 82/02563 A1 | 8/1982 |
| WO | 03/093408 | 11/2003 |
| WO | 2005/116186 | 12/2005 |
| WO | 2010/102059 | 9/2010 |
| WO | 2014/145292 A1 | 9/2014 |
| WO | 2016/024566 A1 | 2/2016 |
| WO | 2017/142958 A1 | 8/2017 |

OTHER PUBLICATIONS

Bancroft et al., "Fluid flow increases mineralized matrix deposition in 3D perfusion culture of marrow stromal osteoblasts in a dose-dependent manner", Proc Natl Acad Sci USA, 99(20), Oct. 1, 2002, 12600-12605 pages.
Bhumiratana, et al., "Controlling Tissue Matrix Assembly of Human Mesenchymal Stem Cells Toward Engineering Native-Like Bone, Cartilage, And Osteochondral Grafts", Columbia University, 2012, 67 pages.
Braccini, et al., "Three-dimensional perfusion culture of human bone marrow cells and generation of osteoinductive grafts", Stem Cells, vol. 23, Issue 8, Sep. 2005, 1066-1072 pages.
Cao, et al., "Transplantation of chondrocytes utilizing a polymer-cell construct to produce tissue-engineered cartilage in the shape of a human ear", Plast Reconstr Surg., Aug. 1997, 100(2):297-302; discussion 303-4.
Ding, et al., "Fabrication of customized anatomical-shaped bone tissue engineering scaffolds with reverse engineering and rapid prototyping technology", Chinese Journal of Clinical Rehabilitation, 2006, vol. 10, Issue 5, pp. 178-181.
Grayson, et al., "Effects of Initial Seeding Density and Fluid Perfusion Rate on Formation of Tissue-Engineered Bone", Tissue Engineering: Part A vol. 14, Nov. 11, 2008, 1809-1820 pages.
Porter, et al., "Noninvasive image analysis of 3D construct mineralization in a perfusion bioreactor", Biomaterials, 2007, vol. 28, pp. 2525-2533.
Porter, et al., "3-D computational modeling of media flow through scaffolds in a perfusion bioreactor", Journal of Biomechanics, 2005, vol. 38, pp. 543-549.
Warnke et al., "Growth and transplantation of a custom vascularised bone graft in a man", Lancet, 2004, vol. 364, No. 9436, pp. 766-770.
Zhao, et al., "Effects of shear stress on 3-D human mesenchymal stem cell construct development in a perfusion bioreactor system: Experiments and hydrodynamic modeling", Biotechnol Bioeng, vol. 96, Issue 3, Feb. 15, 2007, 584-595 Pages.
Cimetta et al. "Microbioreactor arrays for controlling cellular environments: design-principles for human embryonic stem cell applications", Methods 2009, vol. 47, No. 2, pp. 81-89.
Office Action issued Chinese Application No. 2018800354375 dated Jul. 3, 2020.
European Search Report Issued in EP Application No. 18780768.0 dated Apr. 24, 2020.

(56) References Cited

OTHER PUBLICATIONS

Office Action In Japanese Patent Application No. 2019-559714 dated Mar. 26, 2020.
International Preliminary Report on Patentability dated Oct. 8, 2019 by the International Searching Authority in International Application No. PCT/US2018/026730 (17 pages).
International Search Report and Written Opinion dated Aug. 3, 2018 by the International Searching Authority in International Application No. PCT/US2018/026730 (4 pages).
Jones et al., Journal of Applied Biomaterials & Biomechanics, 2006, vol. 4, No. 3, pp. 172-180.
JP Office Action received in JP Application No. 2020-192398 dated Dec. 13, 2021.

* cited by examiner

SYSTEM AND METHOD FOR SEEDING AND CULTURING

CROSS-REFERENCE TO RELATED APPLICATION

This application is a continuation of U.S. application Ser. No. 16/603,082, filed Oct. 4, 2019, which is a U.S. National Phase of International Patent Application No. PCT/US2018/026730, filed on Apr. 9, 2018, which claims the benefit of U.S. Provisional Application No. 62/483,031, filed Apr. 7, 2017. The entire contents of these applications are incorporated herein by reference in their entirety.

FIELD OF THE INVENTION

The present disclosure relates generally to tissue bioengineering and, more particularly, to methods and systems for seeding and culturing porous scaffold for tissue engineering of bone, cartilage, ligament, muscle, fat, teeth and tendons, among other possibilities.

BACKGROUND

Bioreactor cultivation of human stem cells in an osteogenic scaffold has been shown to support cell survival, differentiation, maturation and deposition of bone matrix, while restricting the development of unwanted lineages and facilitating a continued remodeling and vascularization following transplantation.

However, a traditional method of cultivating the scaffold often involves operations manually performed by a laboratory technician using multiple tools or devices, including soaking the scaffold in a media in a Petri dish, drying the scaffold, placing cells onto the scaffold and soaking the scaffold in a media bath to encourage cell growth. As such, there is a need for a cost-efficient and simplified mechanism to handle the cultivation of the scaffold without intense labor. The disclosed technology described herein addresses this need. In addition, the system described herein enables robust process control and maintenance of sterility by reducing user interaction in the process, SUMMARY The disclosed technology relates to a system for seeding therapeutic active ingredients (TAIs) onto a porous scaffold. The system includes a first chamber for accommodating the scaffold, a TAI storage device for storing TAIs, at least one second chamber for storing TAI media, and a gas inlet for receiving gas from a compressed source. A flow circuit is coupled to (i) the first chamber, (ii) the TAI storage device, (iii) the second chamber and (iv) the gas inlet. The flow circuit delivers the TAIs, the TAI media and the gas to the scaffold. A pump pumps at least one of the TAIs, the TAI media and the gas in the flow circuit. The system also includes a plurality of valves for regulating the delivery of the TAIs, the TAI media and the gas to the scaffold.

In some embodiments, the flow circuit includes a media supply line and a media return line between the first chamber and the second chamber, a TAI supply line connected to the TAI storage device for delivering the TAIs, and a gas supply line connected to the gas inlet for delivering the gas.

In some embodiments, the plurality of valves include a media valve for regulating the delivery of the TAI media from the second chamber to the scaffold, a gas valve for regulating the delivery of the gas from the gas inlet, a TAI valve for regulating the delivery of the TAIs from the TAI storage device, a first chamber valve for regulating the delivery of the gas to the first chamber, and a waste valve for regulating a flow from the first chamber.

In some embodiments, the system includes a processor for regulating seeding and culturing of the scaffold by switching one or more valves between open and closed positions. The processor is configured to adjust a pump speed by the pump.

In some embodiments, the processor regulates treating the scaffold with the TAI media by operating the valves to control flow of the TAI media and the TAIs.

In some embodiments, the processor regulates removing an excessive amount of the TAI media from the scaffold with gas by adjusting the valves such that the gas valve, the first chamber valve and the waste valve are in an open position while remaining valves are in a closed position.

In some embodiments, the processor regulates pulsing pressurized gas bursts through the scaffold by repeatedly alternating each of the gas valve, the first valve and the waste valve between an open position and a closed position while remaining valves are in a closed position.

In some embodiments, the processor switches the gas valve to an open position and the first chamber valve to a closed position to generate pressurized gas prior to releasing a pressurized gas burst.

In some embodiments, the processor switches the gas valve to a closed position and the first chamber to an open position to release the pressurized gas burst into the first chamber.

In some embodiments, the processor regulates releasing the TAIs from the TAI storage device by adjusting the valves such that the TAI valve and the waste valve are in an open position while remaining valves are in a closed position.

In some embodiments, the processor regulates pumping the TAIs into the first chamber by adjusting the valves such that the media valve, the first chamber valve and the waste valve are in an open position while remaining valves are in a closed position.

In some embodiments, the system includes a scaffold turner, driven by a motor (which include various types of motors such as rotary actuator, stepper, brushed, brushless, pneumatic, hydraulic, etc.), for rotating the scaffold accommodated in the first chamber through a plurality of positions.

In some embodiments, the processor regulates TAI adhesion on the scaffold by instructing the motor that drives the scaffold turner to rotate the scaffold through the plurality of positions.

In some embodiments, the system includes a motor for driving the pump.

In some embodiments, the processor regulates TAI culturing by instructing the motor that drives the pump to pump the TAI media into the first chamber for a predetermined period of time.

In some embodiments, the graft includes one or more of the following tissues: bone, cartilage, ligament, muscle, fat, skin, nerves, lymph nodes, bone marrow, teeth and tendons. In certain embodiments, the graft is a bone graft.

In some embodiments, the compressed source provides $CO_2$, $N_2$ or mixed gases.

Another aspect of the disclosed technology relates to a method for seeding and culturing TAIs into a porous scaffold. The method includes accommodating a scaffold in a first chamber. A flow circuit delivers TAIs, TAI media and gas to the scaffold from a TAI storage device, at least one second chamber and a gas inlet. A pump pumps at least one of the TAIs, the TAI media and the gas in the flow circuit. A processor regulates the delivery of the TAIs, the TAI media and the gas to the scaffold via a plurality of valves.

In some embodiments, the plurality of valves include a media valve for regulating the delivery of the TAI media from the second chamber, a gas valve for regulating the delivery of the gas from the gas inlet, a TAI valve for regulating the delivery of the TAIs from the TAI storage device, a first chamber valve for regulating the delivery of the gas to the first chamber, and a waste valve for regulating a flow from the first chamber.

In some embodiments, the processor regulates pulsing pressurized gas bursts through the scaffold by repeatedly alternating each of the gas valve, the first chamber valve and the waste valve between an open position and a closed position while remaining valves are in a closed position.

In some embodiments, the processor switches the gas valve to an open position and the first chamber valve to a closed position to generate pressurized gas prior to releasing a pressurized gas burst.

In some embodiments, the processor switches the gas valve to a closed position and the first chamber valve to an open position to release the pressurized gas burst into the first chamber.

In some embodiments, the graft includes one or more of the following tissues: bone, cartilage, ligament, muscle, fat, skin, nerves, lymph nodes, bone marrow, teeth and tendons. In certain embodiments, the graft is a bone graft.

A further aspect of the disclosed technology relates to a method of treating a surface of a porous scaffold. The method includes using liquid and gas pressure to wet and coat the surface of the porous scaffold with a thin layer to facilitate wicking of a cell solution, resulting in a uniform seeded scaffold.

In some embodiments, the method includes accommodating the porous scaffold in a first chamber; delivering TAIs, TAI media and gas to the scaffold via a flow circuit from a TAI storage device, at least one second chamber and a gas inlet; pumping at least one of the TAIs, the TAI media and the gas in the flow circuit by a pump; and regulating the delivery of the TAIs, the TAI media and the gas to the scaffold by a processor via a plurality of valves.

Another aspect of the disclosed technology relates to a preassembled kit for integration into an automated system for scaffold seeding and culturing. The preassembled kit includes a scaffold, a first chamber for accommodating the scaffold, a second chamber for storage purposes, and a flow circuit for connecting the bioreactor with the reservoir. The scaffold, the first chamber, the second chamber and the flow circuit are assembled to form an input to the automated system for scaffold seeding and culturing. The automated system after integration with the preassembled kit includes: the first chamber for accommodating the scaffold; the second chamber for storing TAI media; a therapeutic active ingredient (TAI) storage device for storing TAIs; a gas inlet for receiving gas from a compressed source; the flow circuit coupled to (i) the first chamber, (ii) the TAI storage device, (iii) the second chamber and (iv) the gas inlet, said flow circuit delivering the TAIs, the TAI media and the gas to the scaffold; a pump for pumping at least one of the TAIs, the TAI media and the gas in the flow circuit; and a plurality of valves for regulating the delivery of the TAIs, the TAI media and the gas to the scaffold.

Various aspects of the described example embodiments may be combined with aspects of certain other example embodiments to realize yet further embodiments. It is to be understood that one or more features of any one example may be combined with one or more features of the other example. In addition, any single feature or combination of features in any example or examples may constitute patentable subject matter. Other features of the technology will be apparent from consideration of the information contained in the following detailed description.

BRIEF DESCRIPTION OF THE DRAWINGS

The following Detailed Description of the technology is better understood when read in conjunction with the appended drawings. For the purposes of illustration, there is shown in the drawings exemplary embodiments, but the subject matter is not limited to the specific elements and instrumentalities disclosed. Components in the figures are shown for illustration purposes only, and may not be drawn to scale.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

1. Overview

The present technology relates to engineering a custom-designed autologous graft by cultivating human stem therapeutic active ingredients (TAIs) in an osteogenic scaffold. The TAIs may include one or a combination of the following: cells, drugs, proteins and hydrogel, among other possibilities. The graft may include one or more of the following tissues: bone, cartilage, ligament, muscle, fat, skin, nerves, lymph nodes, bone marrow, teeth and tendons, among other possibilities. A patient specific graft may be designed based on a precise three-dimensional (3D) model of an anatomical defect from a patient's computerized tomography (CT) scan. Using the 3D image, an anatomically-shaped scaffold may be fabricated.

Figure 1:
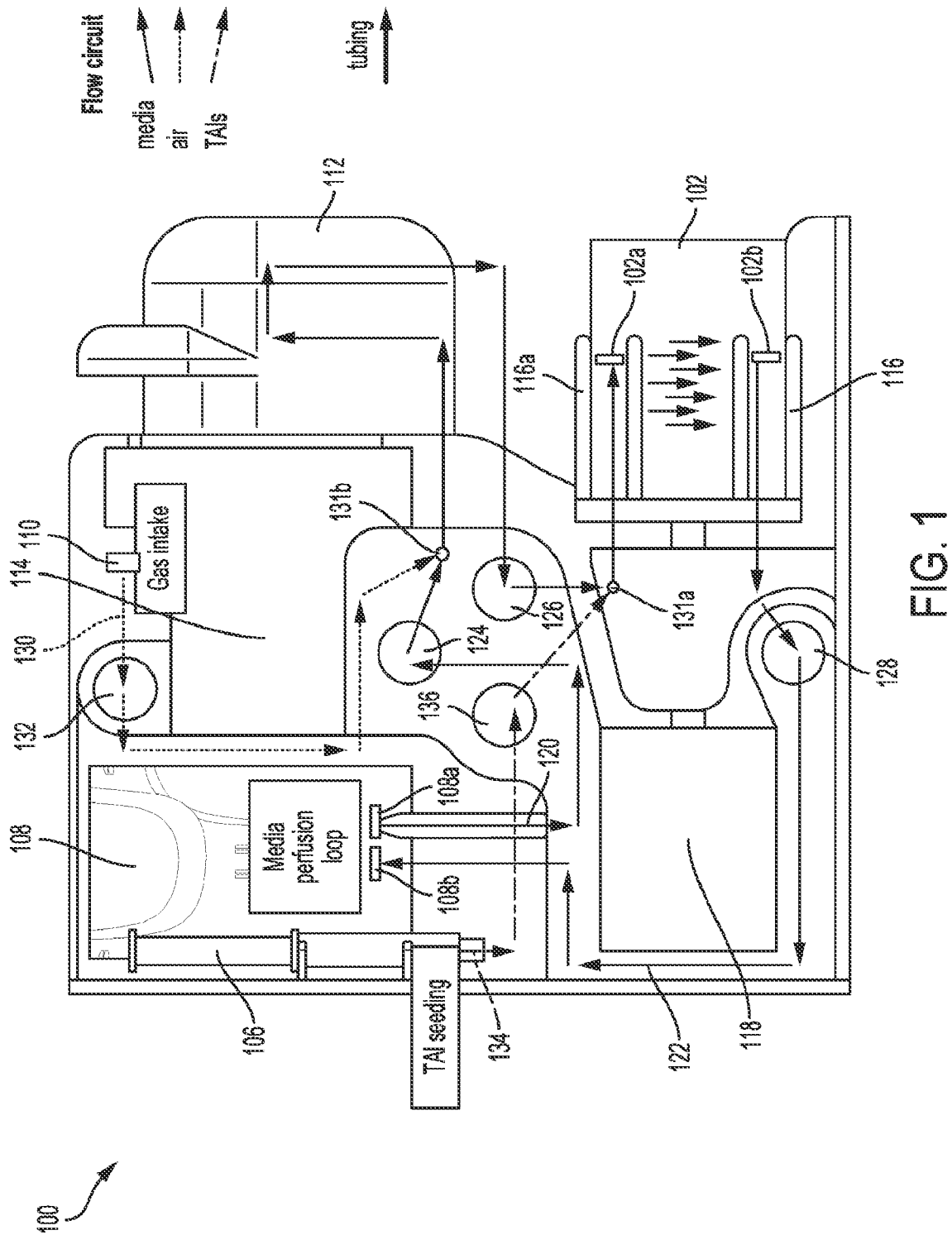
FIG. 1 is a schematic diagram of an automated seeding and culturing system according to one embodiment of the present technology.

The present technology relates a system 100 for cultivating the graft ready for implantation by seeding and culturing the scaffold. FIG. 1 provides a schematic diagram of the system 100 according to one embodiment. The system 100 may be an all-in-one device that handles seeding and culturing of the scaffold. For instance, the system 100 may perform, but is not restricted to, all of the following, pre-wetting the scaffold including gas purging, impregnating the scaffold with TAIs, rotating the scaffold to provide uniform seeding, delivering TAI media to feed the TAIs, and removing wastes produced by the TAIs.

With reference to FIG. 1, the system 100 may include a first chamber 102 that provides an environment for growing a scaffold into a graft. The first chamber may include a mold to accommodate the scaffold. The mold may be custom-built based on the 3D image so as to conform to the configuration of the scaffold.

The system 100 may perfuse the scaffold with TAI s by delivering a TAI solution to the scaffold. The TAI solution may be stored in a TAI storage device 106. The TAI storage device 106 may be a syringe. The TAI solution may include a concentrated suspension of TAIs. The TAIs may be derived or extracted from the patient's own tissue. The TAI solution may be delivered to the first chamber 102 so as to impregnate the scaffold with the TAIs. The TAIs may proliferate in the scaffold and expand into sufficient quantity so as to form a viable graft.

The system 100 may also include one or more second chambers 108 for storing food sources for the TAIs, such as TAI media, to be delivered to the first chamber 102 so as to feed the TAIs. The second chamber 108 may be a TAI media chamber 108. The system 100 may include an gas inlet 110 for receiving gas from a compressed source, and the gas is to be delivered to the first chamber 102. The compressed source may provide $CO_2$, $N_2$ or mixed gases.

The first chamber 102 may include an inlet 102*a* for receiving the TAI media, TAIs, gas for seeding and culturing the scaffold stored therein. The first chamber may include an outlet 102*b* for releasing gas including gas bubbles, excessive TAI media, and wastes produced by the TAIs.

The TAI media chamber 108 may have an outlet 108*a*, coupled to a media supply line 120, for releasing the TAI media to feed TAIs in the first chamber 102. The TAI media chamber 108 may have an inlet 108*b*, coupled to a media return line 122 for receiving TAI media returned from the first chamber 102 as well as the wastes produced by the TAIs in the first chamber 102. The TAI media chamber 108 may store the wastes produced by the TAIs. The TAI media chamber 108 may also receive and collect gas bubbles produced by the first chamber 102 via the media return line 122.

The media supply line 120 may connect the outlet 108*a* of the TAI media chamber 108 to the inlet 102*a* of the first chamber 102. The media supply line 120 may travel through a pump 112, driven by a motor 114, for regulating fluid movement in the media supply line 120. The pump 112 may be a peristaltic pump, a syringe, or a diaphragm pump, among other possibilities. The motor 114 may be chosen from various types of motors such as rotary actuator, stepper, brushed, brushless, pneumatic and hydraulic motors, among other possibilities. Further, the media supply line 120 may travel through a media valve 124 and a first chamber valve 126. Each valve may have an open position to allow a flow through the media supply line 120, and a closed position to block the flow. For example, the media valve 124 may regulate the flow between the TAI media chamber 108 and the pump 112, while the first chamber valve 126 may regulate the flow between the pump 112 and the first chamber 102. The media valve 124 may regulate the delivery of the TAI media from the TAI media chamber 108 chamber to the scaffold.

The media return line 122 may connect the inlet 108*b* of the TAI media chamber 108 to the outlet 102*b* of the first chamber 102. Further, the media return line 122 may travel through a waste valve 128. The waste valve 128 may regulate a flow from the first chamber 102 to the TAI media chamber 108. For example, the waste valve 128 may have an open position to allow the flow through the media return line 120, and a closed position to block the flow. The media return line 122 may convey the TAI media from the first chamber 102 back into the TAI media chamber for reuse.

The TAI storage device 106 may be coupled to a TAI supply line 134. The TAI supply line 134 may travel through a TAI valve 136. The TAI valve 136 may regulate a flow of TAIs in the TAI supply line 134. For example, the TAI valve 136 may have an open position to allow the flow of TAIs through the TAI supply line 134, and a closed position to block the flow of TAIs. The TAI supply line 134 may meet the media supply line 120 at a coupling point 131*a*, where the TAIs from the TAI supply line 134 flow into the media supply line 120.

The gas inlet 110 may be a sterile gas filter such as a PTFE membrane or a high-efficiency particulate air (HEPA) filtered inlet. The gas inlet 110 may be temperature and atmosphere controlled. The gas inlet 110 may be coupled to a gas supply line 130. The gas supply line 130 may travel through a gas valve 132. The gas valve 132 may regulate the gas flow in the gas supply line 130. For example, the gas valve 132 may have an open position to allow the gas flow through the gas supply line 130, and a closed position to block the gas flow. The gas supply line 130 may meet the media supply line 120 at a coupling point 131b, where the gas from the gas supply line 130 flows into the media supply line 120. When the media supply line 120 carries the gas, the pump 112 and the first chamber valve 126 may charge and purge gas to and from the first chamber 102.

The lines 120, 122, 130 and 134 described herein may be soft tubes such as platinum cured silicone tubes. The lines 120, 122, 130 and 134 may form a flow circuit. The valves 124, 126, 128, 132 and 136 described herein may be solenoid valves, such as pinch valves. The valves may control flow through the lines or through the flow circuit. In one embodiment, the pinch valves may squeeze the soft tubes so as to restrict flow through the soft tubes.

Figure 2:
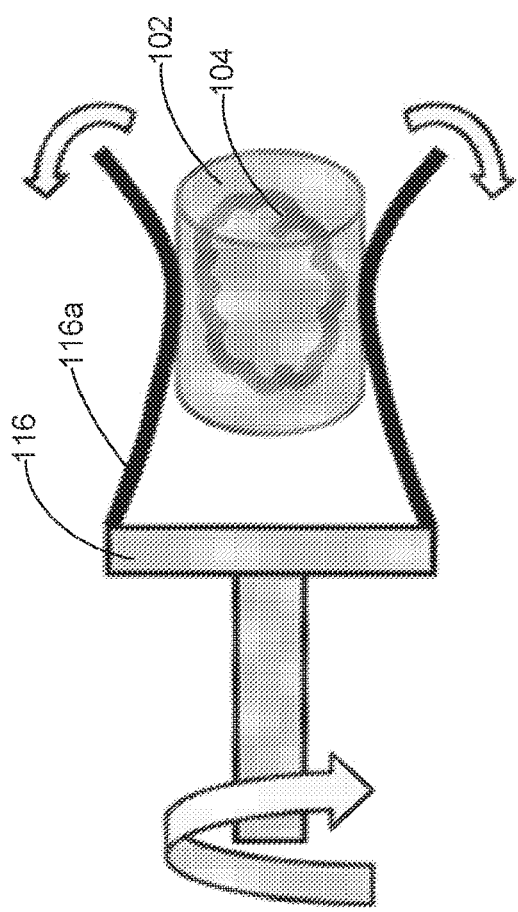
FIG. 2 is a schematic illustration of turning mechanism by a scaffold turner according to one embodiment of the present technology.

The system 100 may include a scaffold turner or rotary holder 116. The scaffold turner 116 may serve as a clamp for holding the first chamber 102. The scaffold turner 116 may have flexible arms 116a so as to hold first chambers of various configurations, such as various geometries. The scaffold turner 116, driven by a motor 118, may rotate the first chamber 102 so as to enable uniform scaffold seeding. The motor 118 may be chosen from various types of motors such as rotary actuator, stepper, brushed, brushless, pneumatic and hydraulic motors, among other possibilities FIG. 2 provides a schematic illustration of the scaffold turner 116 in action which rotates the first chamber 102 as well as the scaffold 104 contained therein.

Figure 3:
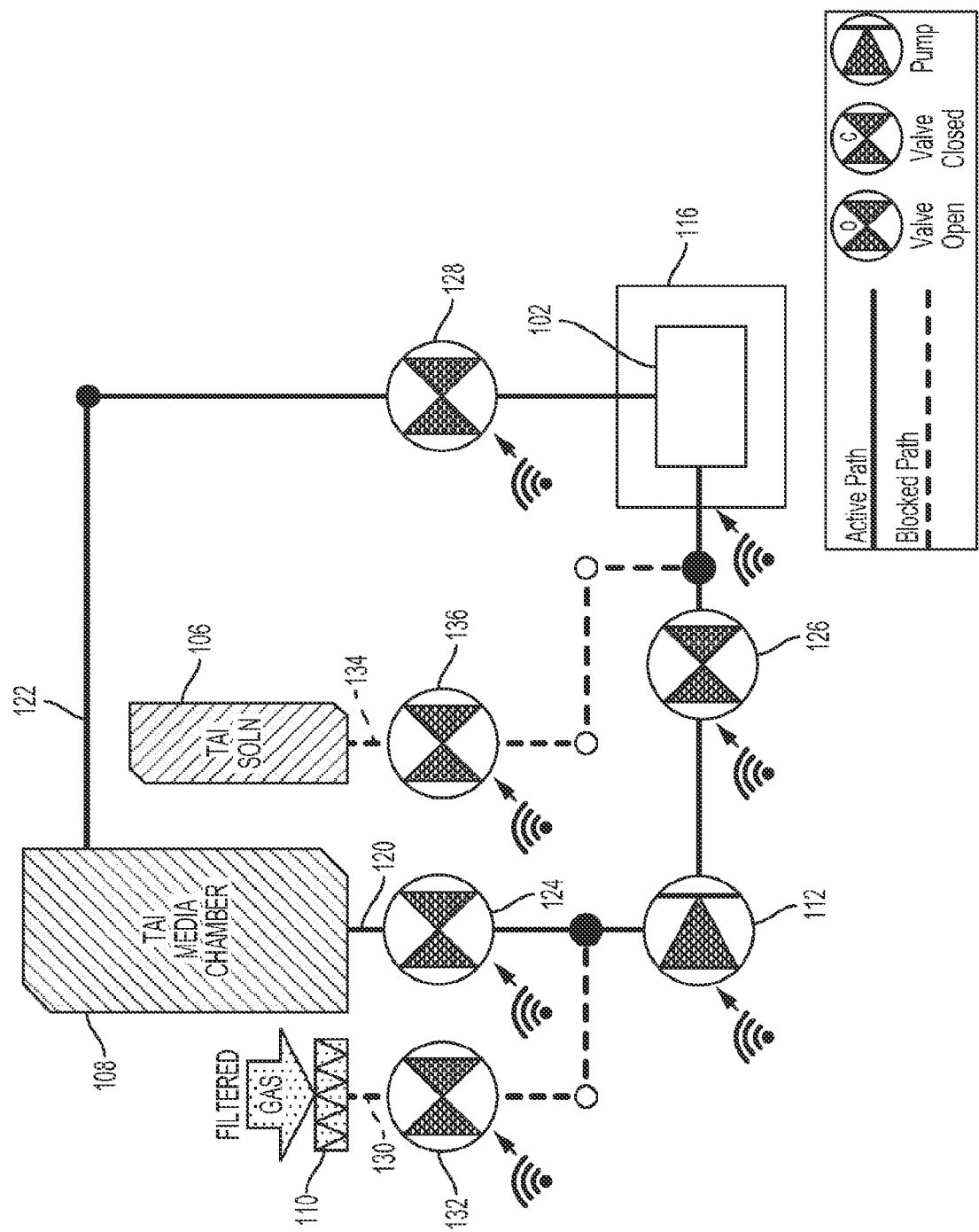
FIG. 3 is a schematic diagram of a fluid circuit of the automated seeding and culturing system according to one embodiment of the present technology.

FIG. 3 is a schematic diagram of a fluid circuit of the system 100 according to one embodiment of the present technology. In FIG. 3, three separate inputs including the gas, TAI media and TAI solution are respectively introduced from the gas inlet 110, the TAI media chamber 108, and the TAI storage device 106 into the first chamber 102 that houses the scaffold. Each of these inputs may be isolated from the first chamber 102 by one or more dedicated valves. For example, the gas, TAI media and TAI solution may be isolated from the first chamber 102 by the gas valve 132, the media valve 124, and the TAIs valve 136, respectively. The pump 112 and the first chamber valve 126 may charge and purge gas to and from the first chamber 102. The waste valve 128 may regulate flow from the first chamber 102 to the TAI media chamber 108.

Figure 4:
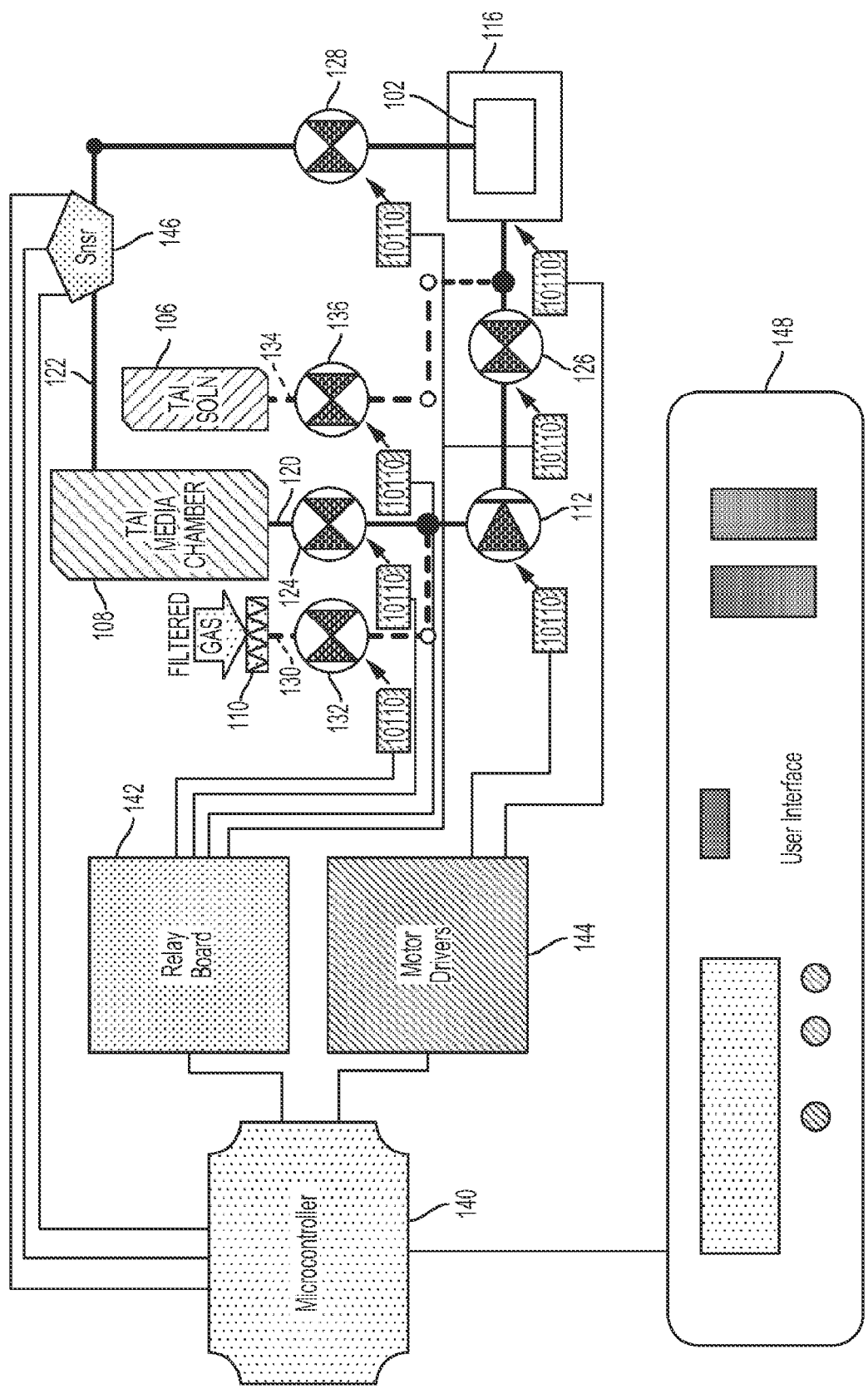
FIG. 4 is a schematic diagram of an electrical circuit coupled to the fluid circuit of the automated seeding and culturing system according to one embodiment of the present technology.

FIG. 4 is a schematic diagram of an electrical circuit coupled to the fluid circuit of the system 100 according to one embodiment of the present technology. As illustrated in FIG. 4, operations of each valve 124, 126, 128, 132 and 136 may be controlled by a processor or microcontroller 140. The processor 140 may include pre-loaded code, which may be uploaded or edited by a user via a user interface 148. The processor 140 may receive geometric properties, such as void volumes, of the scaffold 104 and the first chamber 102. Such information may be provided by the user via the user interface 148. Based on the geometric properties, the processor 140 may determine time for switching each valve between its open and closed positions so as to control the flow, and instruct each valve to perform switching via a relay board 142.

Further, the processor 140 may control the motor 114 that drives the pump 112, and the motor 118 that drives the scaffold turner 116. The processor may determine parameters for operating the motors, and communicate with the motors via their respective motor drivers 144. The processor may adjust a pump speed by the pump 112.

The system 100 may include one or more sensors or sampling ports 146 for taking chemical and physical readings or samples from the flow in the system 100. The processor 104 may analyze the readings to determine if the system 100 has experienced any failure. The processor 104 may also rely on the readings to generate experimental data.

The user interface 148 may provide a screen which displays operation information of the system 100. The user interface 148 may also provide switches for receiving user inputs. The user interface 148 may have a USB port for receiving algorithms to control the system 100.

For simplicity purposes, a power supply is not illustrated in FIG. 4.

2. Seeding and Culturing Processes

The system 100 may regulate seeding and culturing of the scaffold according to embodiments described below.

2.1 Initialization

At initialization, the processor 140 may be set with constant parameters for operating the motors 114 and 118 in accordance with motor specifications. Pins for the processor 140 may also be initialized. At initialization, the processor 104 may also be set with seeding parameters, such as variables describing how long media is cycled, the first chamber rotation rate and positions, and pressurization time. Further, the processor 104 may be set with pump speeds and pump volumes for different functions. Motor positions and program locations may also be initialized.

At initialization, the processor 140 may switch all valves to their closed positions. The user interface 148 may display instructions to the user, such as the following: (1) ask the user to load the first chamber 102 and the lines 120, 122, 130 and 134, (2) ask the user to unlock the media flow, (3) ask the user to enter the first chamber type. Based on the first chamber type, the processor may determine the volume of the first chamber and the flow rate for perfusing the TAI media. In one embodiment, the volume of the first chamber and the flow rate may be provided by the user.

2.2 Seeding

The seeding process may include (1) a pre-wetting process (phases 1-3 described below), (2) a TAI delivery process (phases 4-5 described below), and (3) a TAI adhesion process (phase 6 described below).

Figure 5:
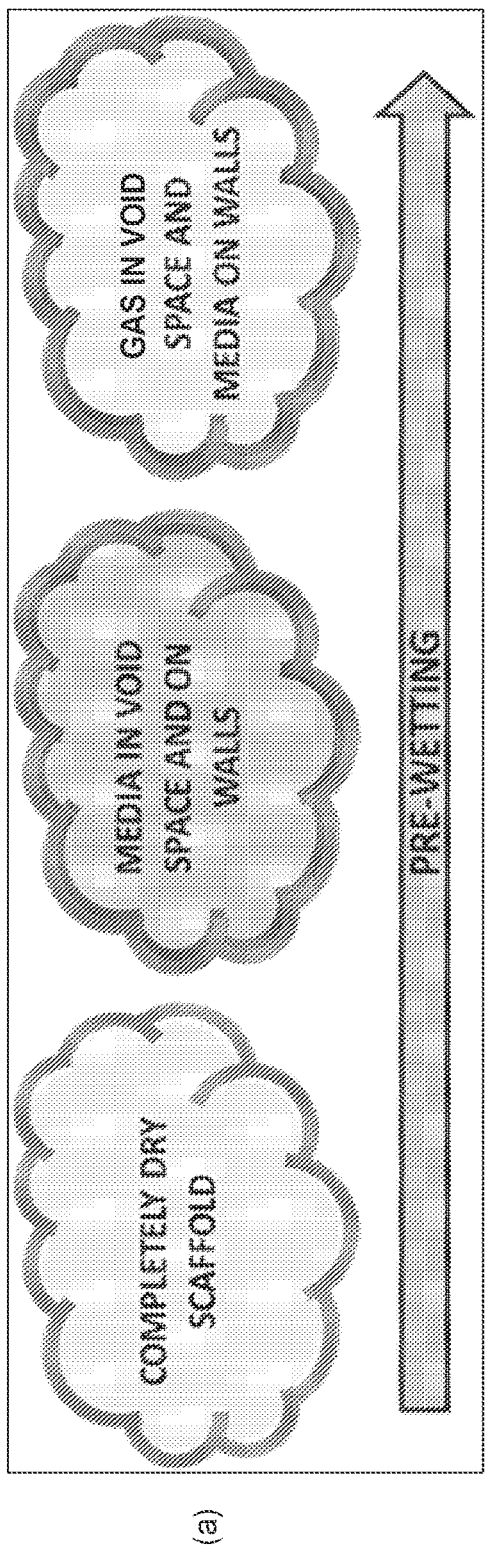
FIG. 5 is a schematic illustration of a scaffold during (a) a pre-wetting process and (b) a TAI delivery and adhesion process according to one embodiment of the present technology.
Figure 5:
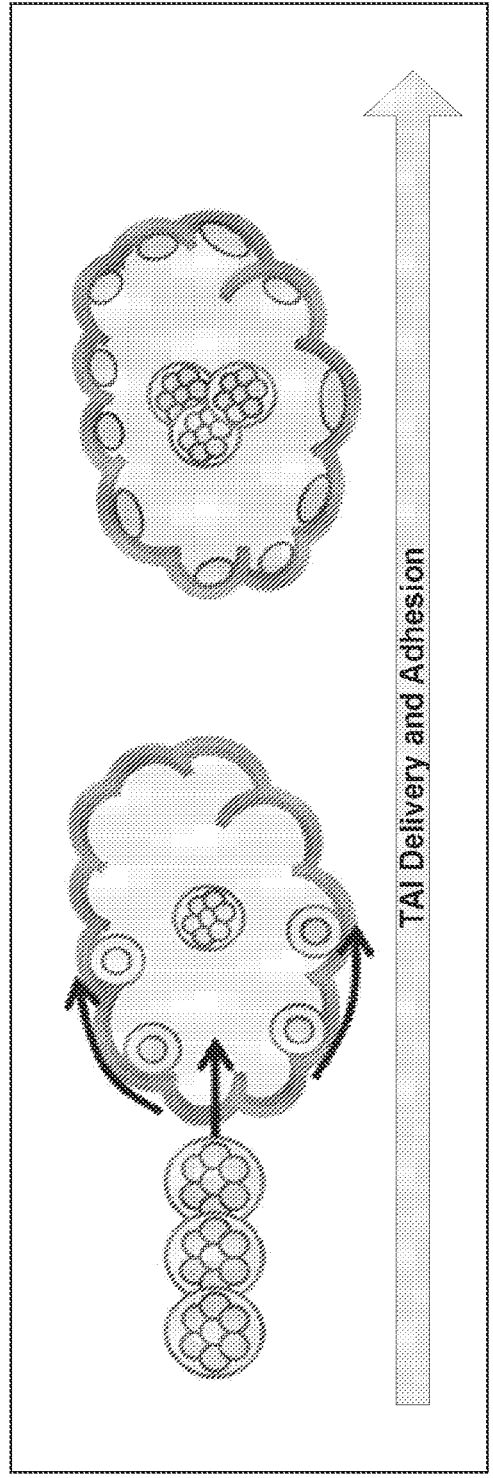

As shown in FIG. 5, during the pre-wetting process, TAI media is delivered into the scaffold and fills void spaces in the scaffold including its walls. As part of the pre-wetting process, gas is introduced into the scaffold and fills void spaces in the scaffold. Pre-wetting is important for TAI adhesion to a scaffold. During the TAI delivery process, TAIs are delivered to the scaffold. During the TAI adhesion process, TAIs may climb into crevices of the pre-wet walls of the scaffold.

The pre-wetting process may wet all inner surfaces of the scaffold. The pre-wetting process may provide benefits for the TAI delivery process and the TAI adhesion process. For example, as a result of the pre-wetting process, the TAI solution may be encouraged to climb into crevices of walls of the scaffold by capillary action and surface tension. Accordingly, the TAI solution may move into hard-to-reach places where the TAI solution otherwise would not travel to through its natural course. As a result, the pre-wetting process ultimately enables the TAI solution to cover and form adhesion with more surface areas of the scaffold. The pre-wetting process is particularly important for scaffolds that have porous structures, as the porous structures contain many roundish cavities with potentially small entrances and sharp features that hinder fluid flow. With the benefit of pre-wetting, inputted TAIs can readily climb into the crevices of the pre-wet walls.

Detailed discussion of each phase of the seeding process is provided below 2.2.1 Phase 1: Media Rinse (Pre-Wet Part 1)

Figure 6:
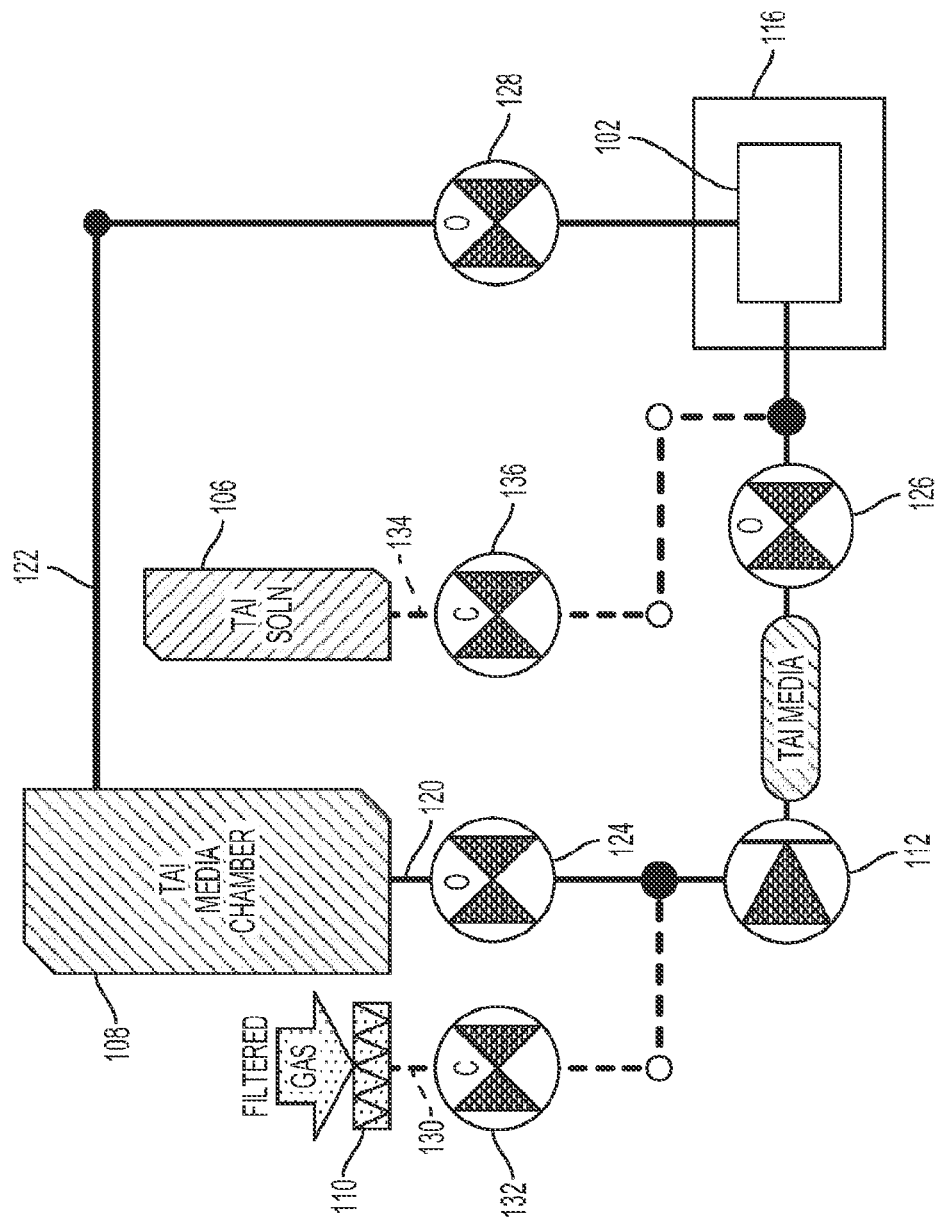
FIG. 6 is a schematic diagram of a circuit configuration of the automated seeding and culturing system to introduce a flow of media into a first chamber according to one embodiment of the present technology.

Prior to the pre-wetting process, a completely dry scaffold may be placed in the first chamber 102. The scaffold may have a 3D porous structure. FIG. 6 illustrates a circuit configuration of the system 100 in the first phase of the pre-wetting process. The processor may regulate treating the scaffold with the TAI media by operating the valves to control flow of the TAI media and the TAIs. As shown in FIG. 6, the processor 140 may switch the media valve 124, the first chamber valve 126, and the waste valve 128 to their open positions, while the gas valve 132 and the TAI valve 136 are in their closed positions. A predetermined amount of the TAI media from the TAI media chamber 108 may be pumped into the first chamber 102 via the pump 112. As the TAI media is pumped into the first chamber 102, the TAI media may fill void spaces in the scaffold including its walls. As a result, the scaffold stored in the first chamber 102 may be rinsed and soaked in the forced flow of TAI media. The forced flow of the TAI media may increase the amount of the surface area of the scaffold wetted by the TAI media. For example, all surfaces of the scaffold may be wetted by the TAI media.

After the TAI media is delivered into the first chamber 102, the processor 140 may switch the media valve 124, the first chamber valve 126 and the waste valve 128 to their closed positions.

2.2.2 Phase 2: Gas Purge 1 (Pre-Wet Part 2)

Figure 7:
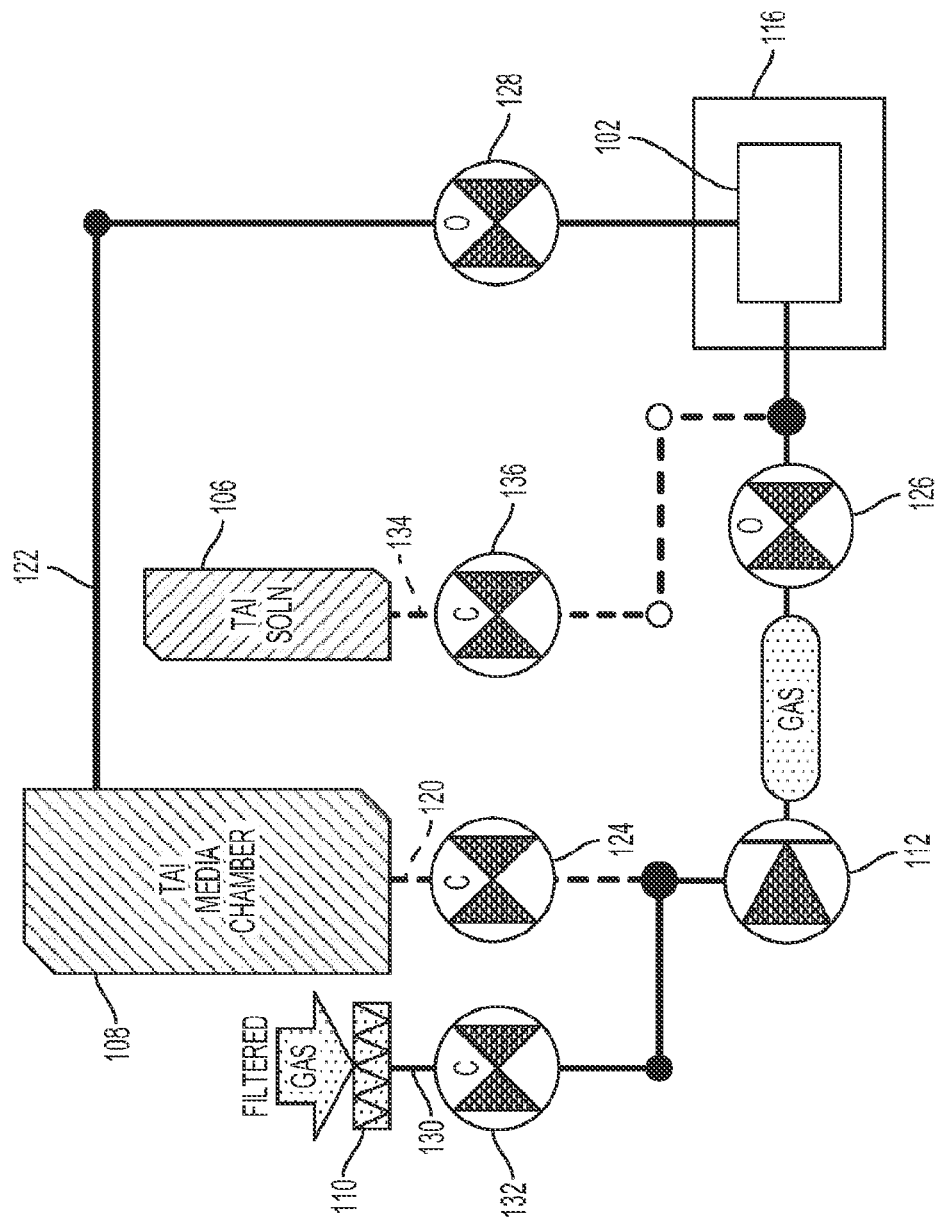
FIG. 7 is a schematic diagram of a circuit configuration of the automated seeding and culturing system to introduce gas into the first chamber according to one embodiment of the present technology.
Figure 13:
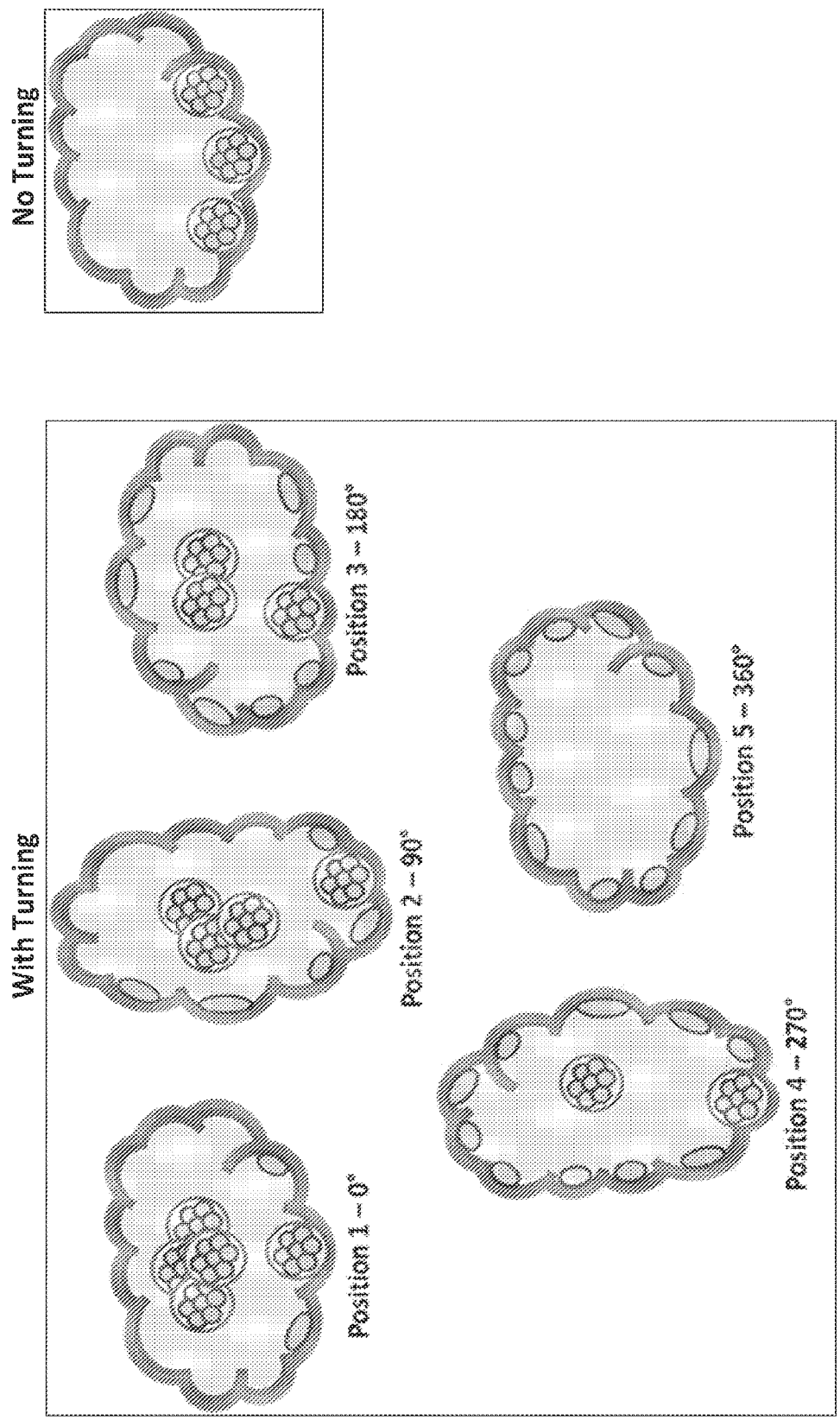
FIG. 13 is a schematic diagram illustrating the scaffold at different rotation positions according to one embodiment of the present technology.
Figure 14:
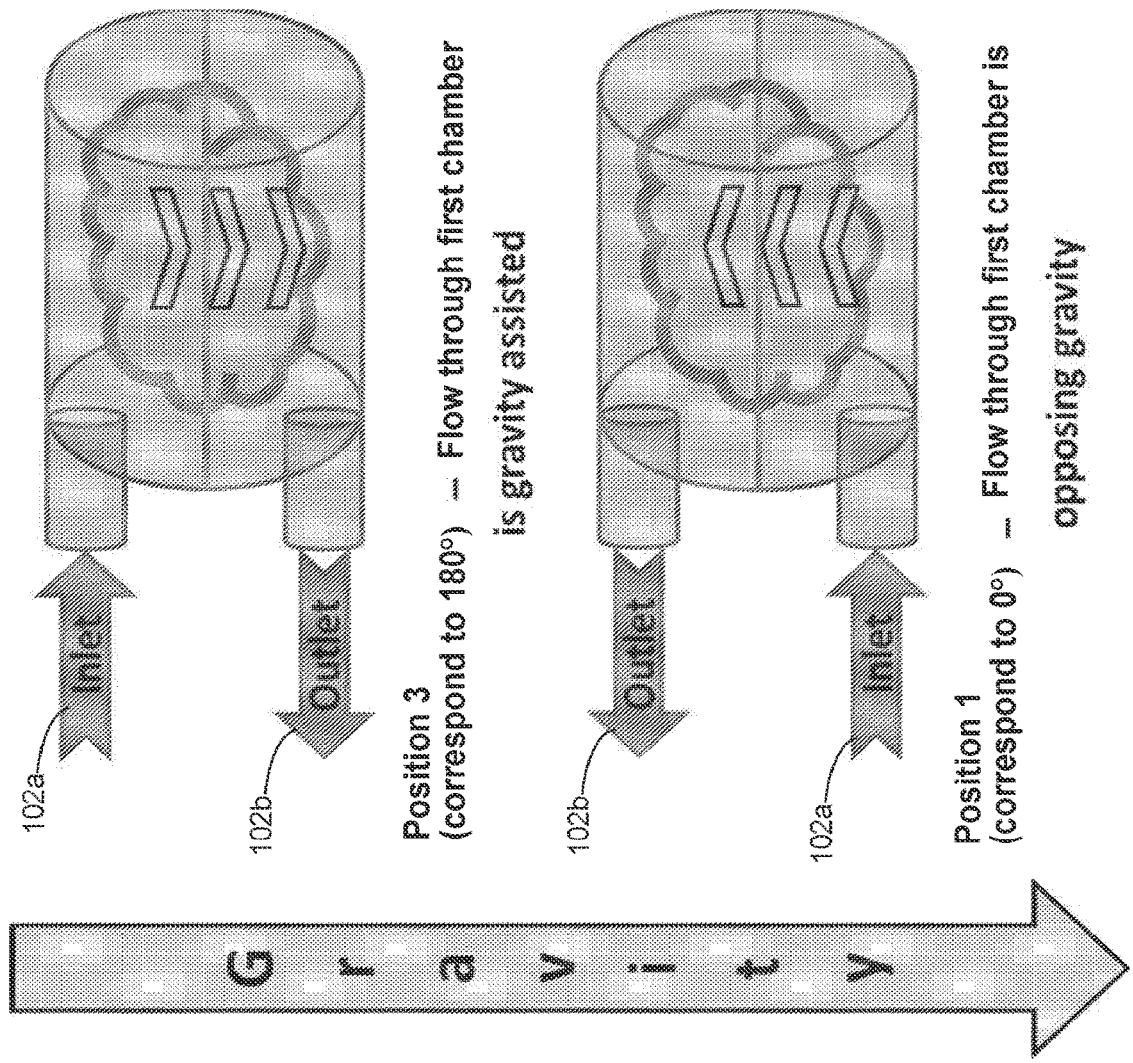
FIG. 14 is a schematic diagram comparing different effects as a result of rotating scaffold to different positions.

FIG. 7 is a schematic diagram of a circuit configuration of the system 100 in the second phase of the pre-wetting process. In this phase, the processor 140 may first, as an optional step, initialize the first chamber position to prevent tube tangling. For example, the processor 140 may instruct the motor 118 to rotate the scaffold turner 116 so as to rotate the first chamber 102 and the scaffold contained therein to a particular position. For example, the first chamber 102 may be rotated to a position as shown in FIG. 1, where the inlet 102a is at the top and the outlet 102b is at the bottom. As a result of the rotation of the first chamber 102, the scaffold contained therein may be rotated to position 3 (180 rotation) as illustrated in FIG. 13, and also illustrated in FIG. 14. As shown in FIG. 14, when the inlet 102a is at the top and the outlet 102b is at the bottom, gravity assists the flow in the first chamber, and helps fluid drainage. In other examples, the first chamber 102 and the scaffold contained therein may be rotated to other suitable positions. This rotation step may be optional, such that the processor 140 may omit the rotation step and start the second phase of the pre-wetting process with the next step.

Next, the processor 140 may open the gas valve 132, the first chamber valve 126 and the waste valve 128. Thereafter, gas from the gas inlet 110 may be pumped into the first chamber via the pump 112. As gas is introduced through the scaffold, excessive TAI media in the void spaces of the scaffold may be removed from the scaffold, and may be returned back to the TAI media chamber 108. As the bulk of the TAI media is removed from the scaffold, a thin layer of the TAI media may remain in inner and outer walls of the scaffold. After a brief period of time, the processor 140 may close the gas valve 132, the first chamber valve 126 and the waste valve 128.

The second phase may facilitate volumetric distribution of TAIs in later phases 2.2.3 Phase 3: Gas Purge 2 (Pre-Wet Part 3)

Figure 8:
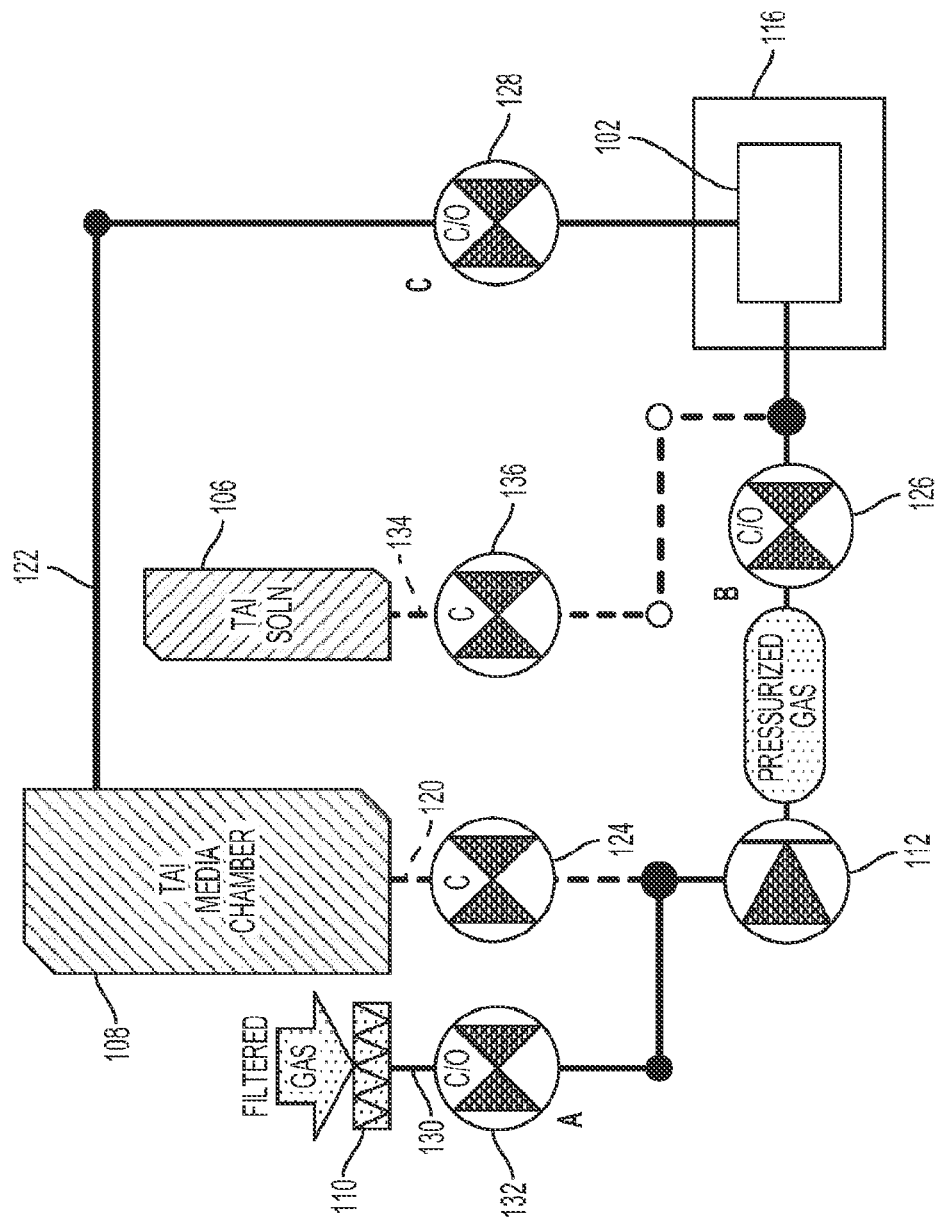
FIG. 8 is a schematic diagram of a circuit configuration of the automated seeding and culturing system to introduce pressurized gas bursts into the first chamber according to one embodiment of the present technology.

FIG. 8 is a schematic diagram of a circuit configuration of the system 100 in the third phase of the pre-wetting process. In this phase, the processor 140 may determine a number of gas bursts.

Each gas purge may include a gas charging step and a gas releasing step. At the gas charging step, the processor 140 may open the gas valve 132 and the waste valve 128 while other valves remain closed. Under the control of the pump 112, gas may flow from the gas inlet 110 into the gas supply line 130. Since the first chamber valve 126 is at its closed position, pressurized gas may be temporarily stored in the line or lines between the gas inlet 110 and the first chamber valve 126. The line or lines that carry the pressurized gas may be made of a flexible material, and may inflate like a balloon when one end is held closed and gas is pushed into it.

At the gas releasing step, the processor 140 may first close the gas valve 132 prior to a gas burst. Then, the processor 140 may open the first chamber valve 126 to release one pulse of a pressurized gas burst into the first chamber 102, while the waste valve 128 remains open. This gas burst may wet the scaffold in the first chamber 102 by strongly compressing the TAI media in the first chamber 102. The gas burst may also eject any lingering TAI media in the void spaces of the scaffold. After a gas burst is released, the processor 140 may close the first chamber valve 126 and the waste valve 128 to prepare for the next gas burst.

The processor 140 may repeatedly alternate the gas charging and releasing steps until the determined number of gas bursts are released. Table I produced below provides an exemplary sequence of valve operations in this third phase

| Function | Valve 132 | Valve 126 | Valve 128 |
| --- | --- | --- | --- |
| Charging | Open | Closed | Open |
| Pre-Burst | Closed | Closed | Open |
| Burst | Closed | Open | Open |
| Pre-Charge | Closed | Closed | Closed |

Figure 9:
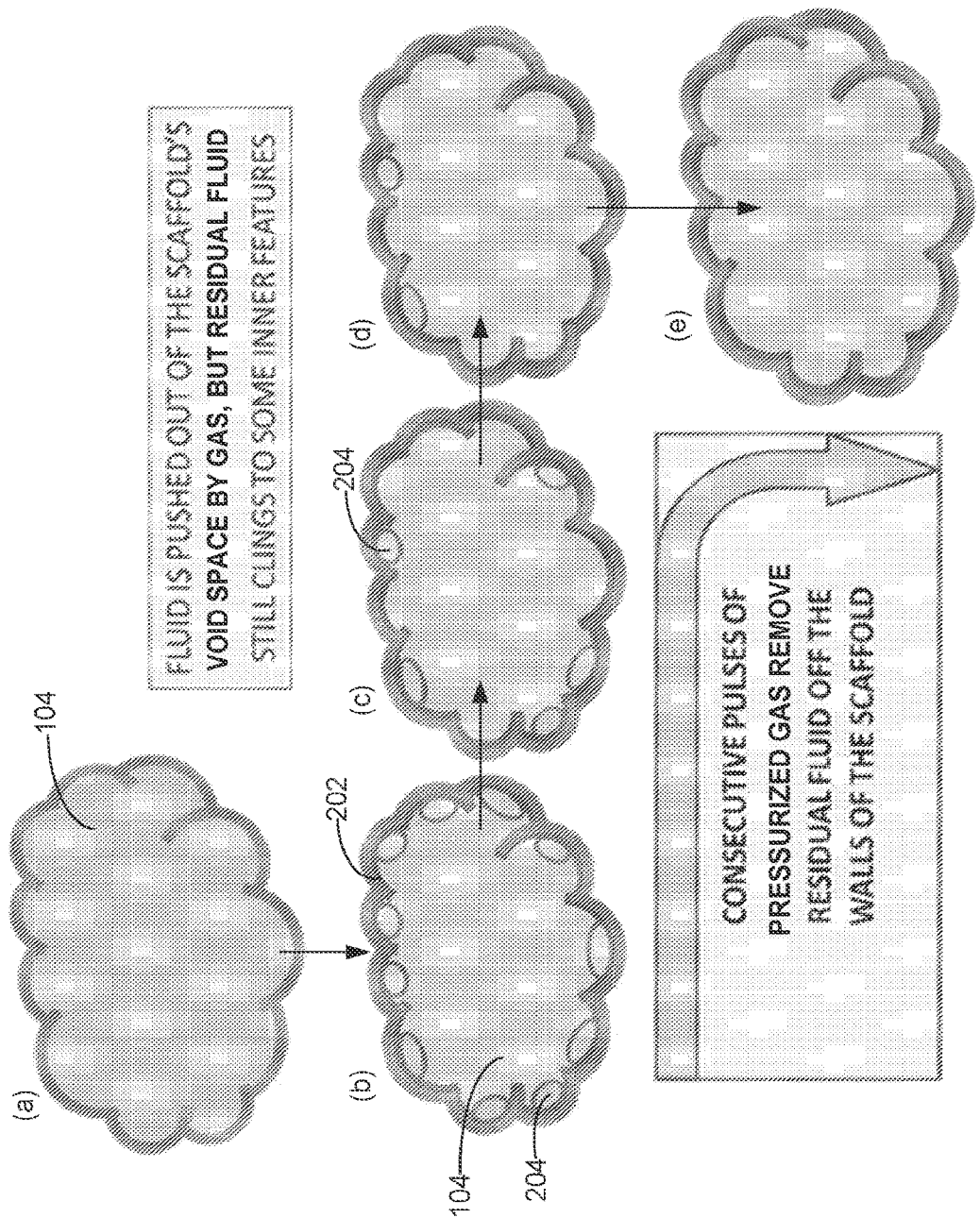
FIG. 9 is a schematic illustration of a scaffold during a pre-wetting process according to one embodiment of the present technology.

FIG. 9 is a schematic illustration of transformation of a scaffold through the three phases of the pre-wetting process. As illustrated in FIG. 9, step (a) represents a scaffold 104 in its completely dry state prior to the pre-wetting process. Step (b) represents the first phase of the pre-wetting process during which the TAI media is introduced into the scaffold 104. A layer 202 of TAI media is formed on a wall of the scaffold 104, along with excessive/residual TAI media 204. Step (c) represents the second phase of the pre-wetting process in which excessive TAI media 204 is removed from void spaces by gas. As illustrated in step (c), some residual TAI media 204 may still cling to some inner surfaces of the scaffold 104. Steps (d) and (e) represent the third phase of the pre-wetting process in which consecutive pulses of pressurized gas may remove residual TAI media off the walls of the scaffold 104.

The method of using gas bursts to eject excessive TAI media and wet the scaffold may provide many advantages. The gas bursts may aid in the removal of fluid in the pore spaces especially the regions with smaller pores which may be more restricted, tortuous and harder to reach. After gas purge, the scaffold pores are free of fluid resulting in open space with wetted surface which may aid the delivery and distribution of the TAI solutions. Casting, painting, and surface coating industries may use sprays, which generally rely on centrifugal forces and gravity, to evenly coat surfaces. Using gas bursts would be inefficient in those industries.

2.2.4 Phase 4: TAI Delivery 1

Figure 10:
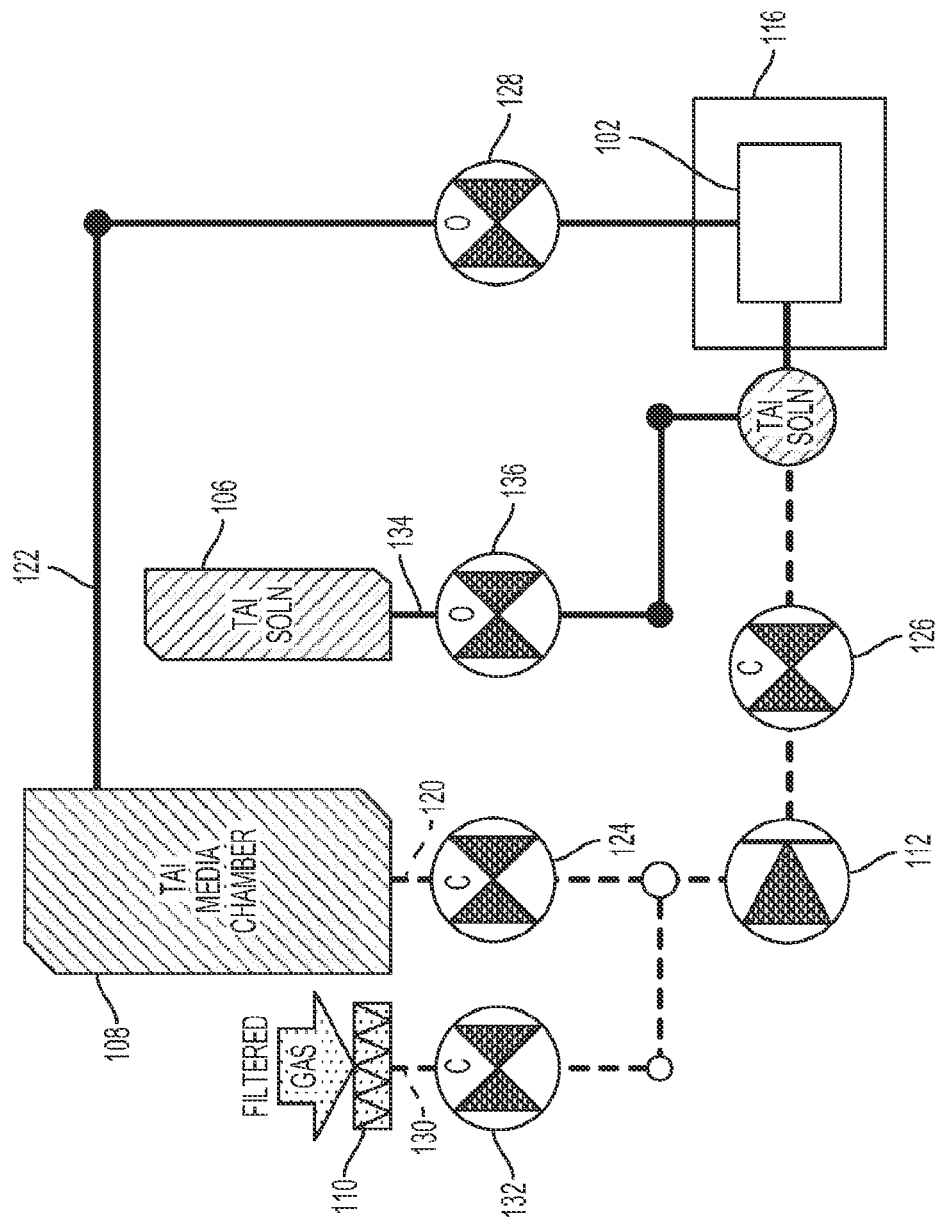
FIG. 10 is a schematic diagram of a circuit configuration of the automated seeding and culturing system to introduce a TAI solution to a point just before the first chamber according to one embodiment of the present technology.

Subsequent to the pre-wetting process, the TAI solution may be introduced into the scaffold through a TAI delivery process. The TAI delivery process may include two phases. FIG. 10 is a schematic diagram of a circuit configuration of the system 100 in the first phase of the TAI delivery process, which also corresponds to phase 4 of the overall seeding and culturing process. In this phase, the processor 140 may, as an optional step, rotate the scaffold turner 116 so as to rotate the first chamber 102 and the scaffold contained therein to a different position. For example, the first chamber 102 may be rotated to a position such that the outlet 102b is at the top, while the inlet 102a is at the bottom. As a result, the scaffold contained therein may be placed to position 1 as illustrated in FIG. 13, and also illustrated in FIG. 14. Such rotation may encourage capillary action, preventing the media from flowing in a single downward direction under gravity. For instance, as shown in FIG. 14, when the outlet 102b is at the top, and the inlet 102a is at the bottom, the TAI media flows through the scaffold's pores under the influence of capillary action, opposing the force of gravity. In other examples, the first chamber 102 and the scaffold contained therein may be rotated to other suitable positions. This rotation step may be optional, such that the processor 140 may omit the rotation step and begin the TAI delivery process with the next step.

At the next step, the processor 140 may open the TAI valve 136 and the waste valve 128. Thereafter, the processor 140 may instruct the user interface 148 to display instructions to the user to inject the TAI solution containing the TAIs from the TAI storage device 106. In one embodiment, instead of manual injection, the TAI solution may be injected via a pump. The TAI solution may flow through the TAI supply line 134, and stop prior to the first chamber 102.

2.2.5 Phase 5: TAI Delivery 2

Figure 11:
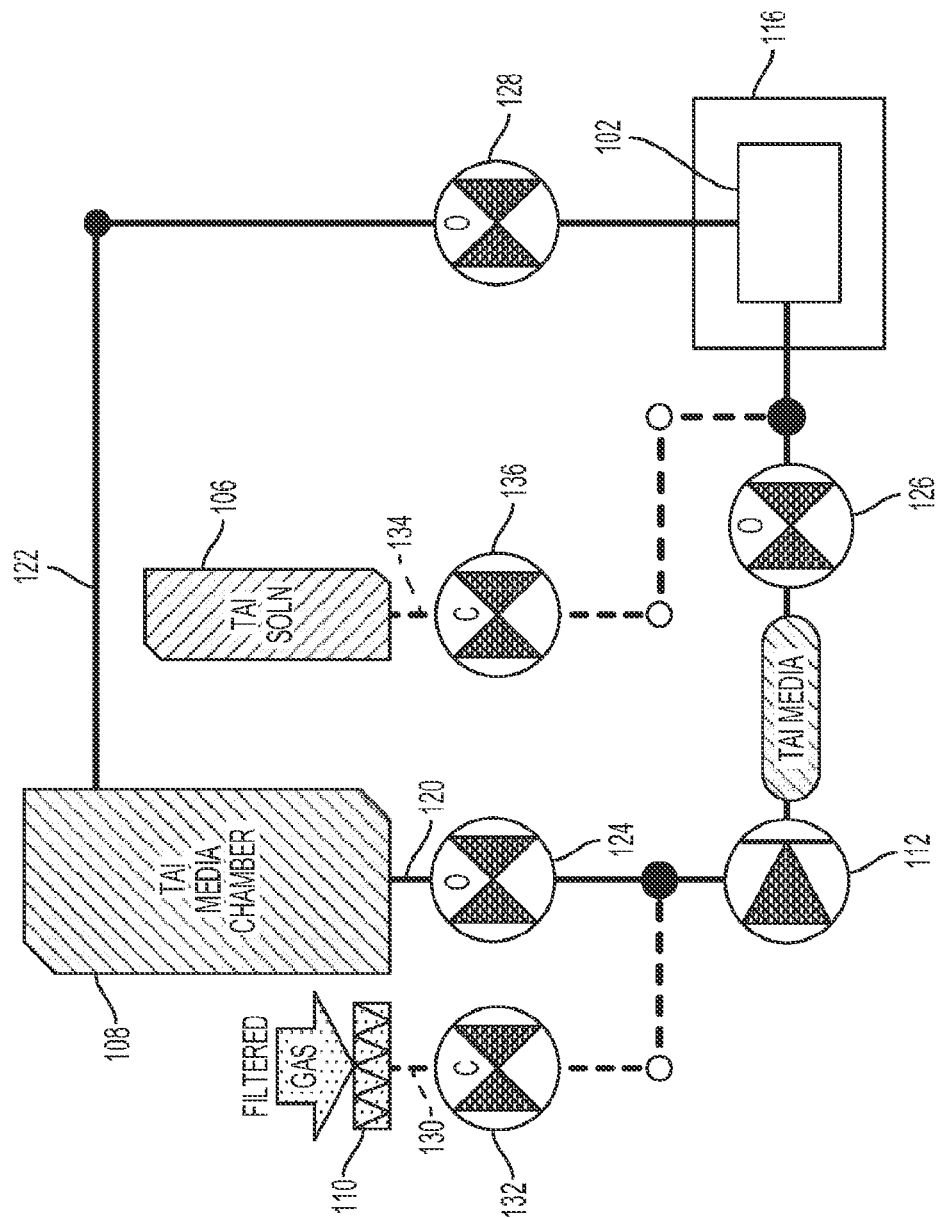
FIG. 11 is a schematic diagram of a circuit configuration of the automated seeding and culturing system to pump the TAI solution into the first chamber according to one embodiment of the present technology.

FIG. 11 is a schematic diagram of a circuit configuration of the system 100 in the second phase of the TAI delivery process, which also corresponds to phase 5 of the overall seeding and culturing process. In this phase, the processor 140 first closes the TAI valve 136, and then opens the medial valve 124 and the first chamber valve 126. Next, the processor 140 may instruct the motor 114 to activate the pump 112. Under the control of the pump 112, the TAI media may flow into the media supply line 120 from the TAI media chamber 108, and push the TAI solution into the first chamber 102. As a result, a concentrated TAI solution may be placed on the scaffold and absorbed into the scaffold. Thereafter, the processor 140 may close the waste valve 128.

During this phase, the TAI solution may be pumped forward and carefully positioned to fill the scaffold volume. This is important for the efficiency of TAI seeding. This phase ensures minimal TAIs are wasted in a location that is not the scaffold.

2.2.6 Phase 6: TAI Adhesion

Figure 12:
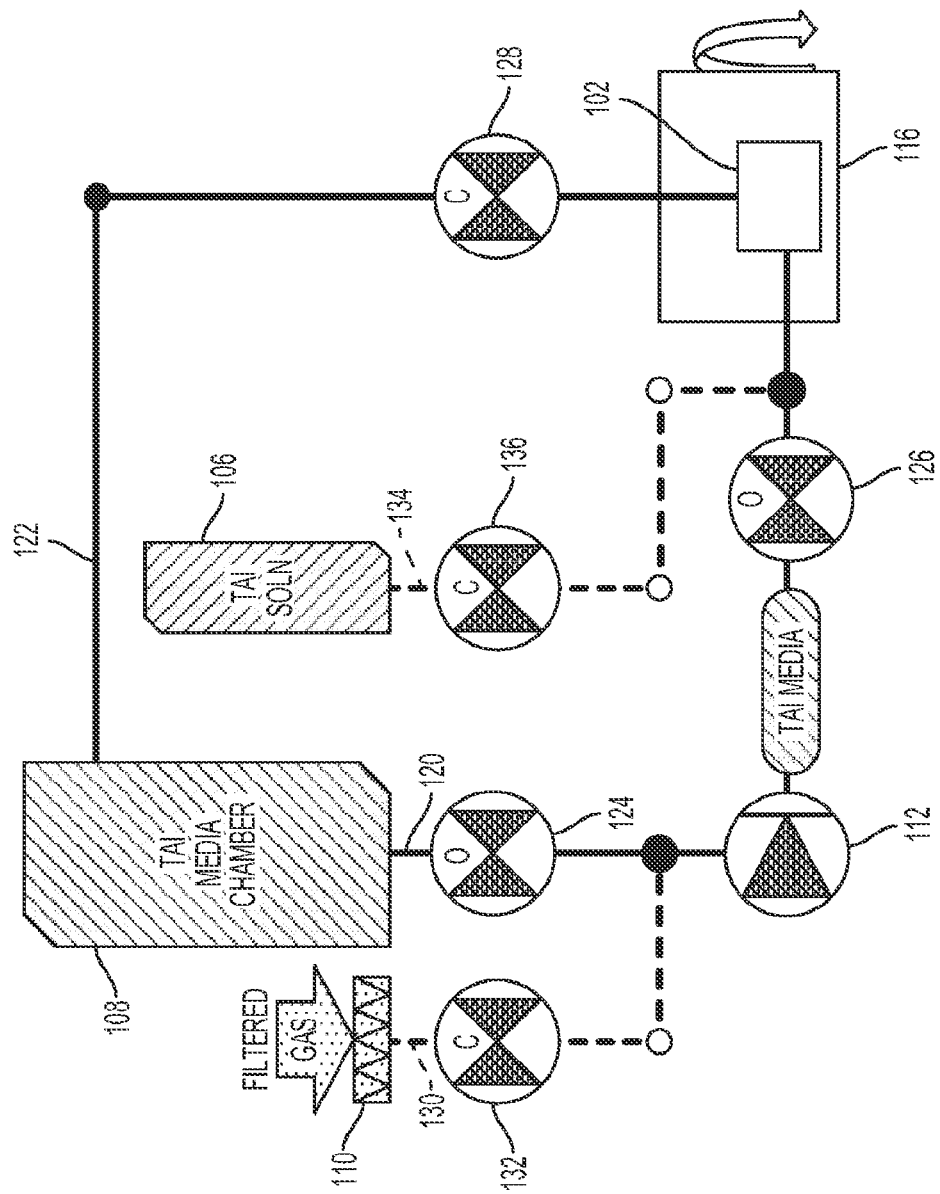
FIG. 12 is a schematic diagram of a circuit configuration of the automated seeding and culturing system to rotate the scaffold through different positions according to one embodiment of the present technology.

Once the TAIs are delivered into the first chamber 102, the TAIs need some time to adhere to the scaffold. This process of placing TAI solution and resting may be done multiple times, and may coordinate with changing the scaffold's orientation. FIG. 12 is a schematic diagram of a circuit configuration of the system 100 for rotating the scaffold through different positions. In this phase, the waste valve 128 remains closed, and the first chamber 102 stays in a closed condition. The processor 140 may instruct the motor 118 to rotate the scaffold turner 116 so as to periodically rotate the scaffold through various positions. By rotating the scaffold through various positions, TAIs may be distributed over different areas of the scaffold to compensate for gravitational bias. For examples, TAIs that are not attached to any area of the scaffold may fall to other areas of the scaffold that do not yet have TAIs. The scaffold turner 116 may repeat the rotation multiple times. In one embodiment, the scaffold turner 116 may periodically move back and forth in 180 degrees, and stay static for a period of time between motions to let the TAIs settle or allow the TAIs to form attachments with the scaffold.

FIG. 13 is a schematic diagram illustrating exemplary positions of the scaffold according to one embodiment. For instance, the scaffold may be rotated or turned through five distinct positions, including a 0-degree rotation corresponding to position 1, a 90-degree rotation corresponding to position 2, a 180-degree rotation corresponding to position 3, a 270-degree rotation corresponding to position 4 and a 360-rotation corresponding to position 5. As illustrated in FIG. 13, with the rotation or turning mechanism, uniform distribution and attachment of the TAIs over the scaffold is achieved, avoiding irregular distribution of the TAIs which otherwise would occur in the absence of the rotation or turning mechanism. The degree of rotation may be defined with respect to the bioreactor 102. For example, as shown in FIG. 14, the 180-degree rotation may correspond to a position where the inlet 102a is at the top, while the outlet 102b is at the bottom. The 0-degree rotation may correspond to a position where the inlet 102a is at the bottom, while the outlet 102b is at the top.

In one embodiment, while the waste valve 128 remains closed, the first chamber 102 may be pressurized periodically by pumping the TAI media against the closed waste valve 128.

The above phases (phase 1 to phase 6) complete the seeding process.

2.3 Phase 7: TAI Culturing

As a result of the TAI seeding process, the TAIs may form sufficient attachments with the scaffold. As nutrients are consumed by the TAIs, wastes are also produced by the TAIs. The TAI media inside the first chamber 102 thus needs to be refreshed from time to time. For that reason, the system 100 may enter a TAI culturing phase to refresh the TAI media periodically and also to continue the perfusion period. The TAI culturing phase may last for a period of weeks.

Figure 15:
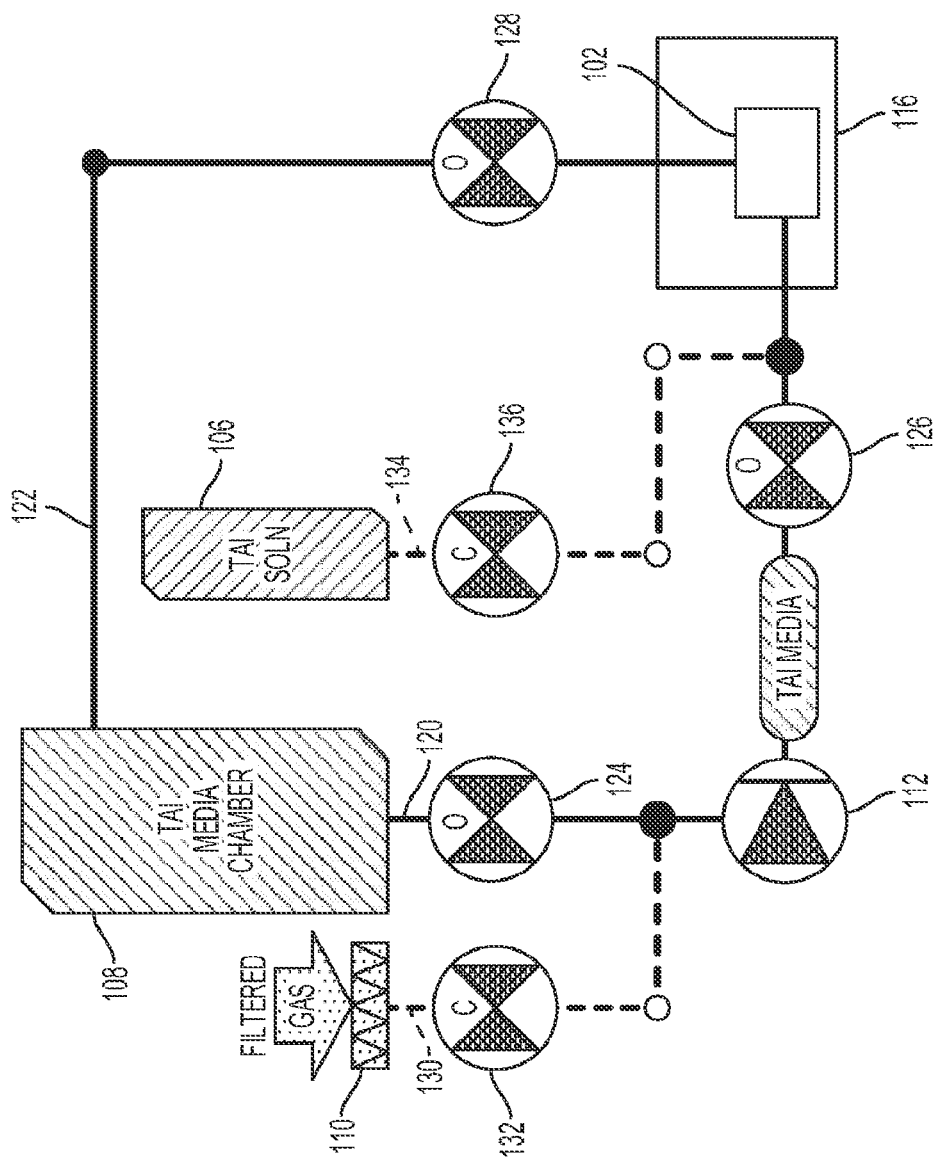
FIG. 15 is a schematic diagram of a circuit configuration of the automated seeding and culturing system to introduce continuous media flow into the first chamber during a culturing process according to one embodiment of the present technology.

FIG. 15 is a schematic diagram of a circuit configuration of the system 100 in the TAI culturing phase. In this phase, the processor 140 may repeatedly refresh the TAI media from time to time. The processor 140 may perform the following steps to refresh the TAI media each time.

The processor 140 may first close all valves. Next, the processor 140 may instruct the motor 118 to rotate the scaffold turner 116 so as to rotate the scaffold to a particular position. For example, the scaffold may be placed to position 3 as illustrated in FIG. 13, or other suitable positions. Thereafter, the processor 140 may open the waste valve 128, the first chamber valve 126 and the media valve 124. Next, the processor 140 may activate the motor 114 for the pump, and pump the TAI media from the TAI media chamber 108 into the first chamber 102 for a predetermined period of time. During this predetermined period of time, the TAI media may be changed.

Once the predetermined period of time lapses, the processor 140 may perform one or more of the following: (1) reverse the media flow to perfuse the scaffold with different flow directions, (2) instruct the motor 118 to rotate the scaffold turner 116 so as to rotate the scaffold to another position, e.g., position 0 as illustrated in FIG. 13, or other suitable positions, (3) stop pumping, and (4) close all valves. By rotating the scaffold to various positions, media may flow to various locations within the scaffold to encourage uniform TAI growth, avoiding TAI growth in one concentrated location that may otherwise occur in the absence of rotation.

3 Alternative Embodiments

Figure 16:
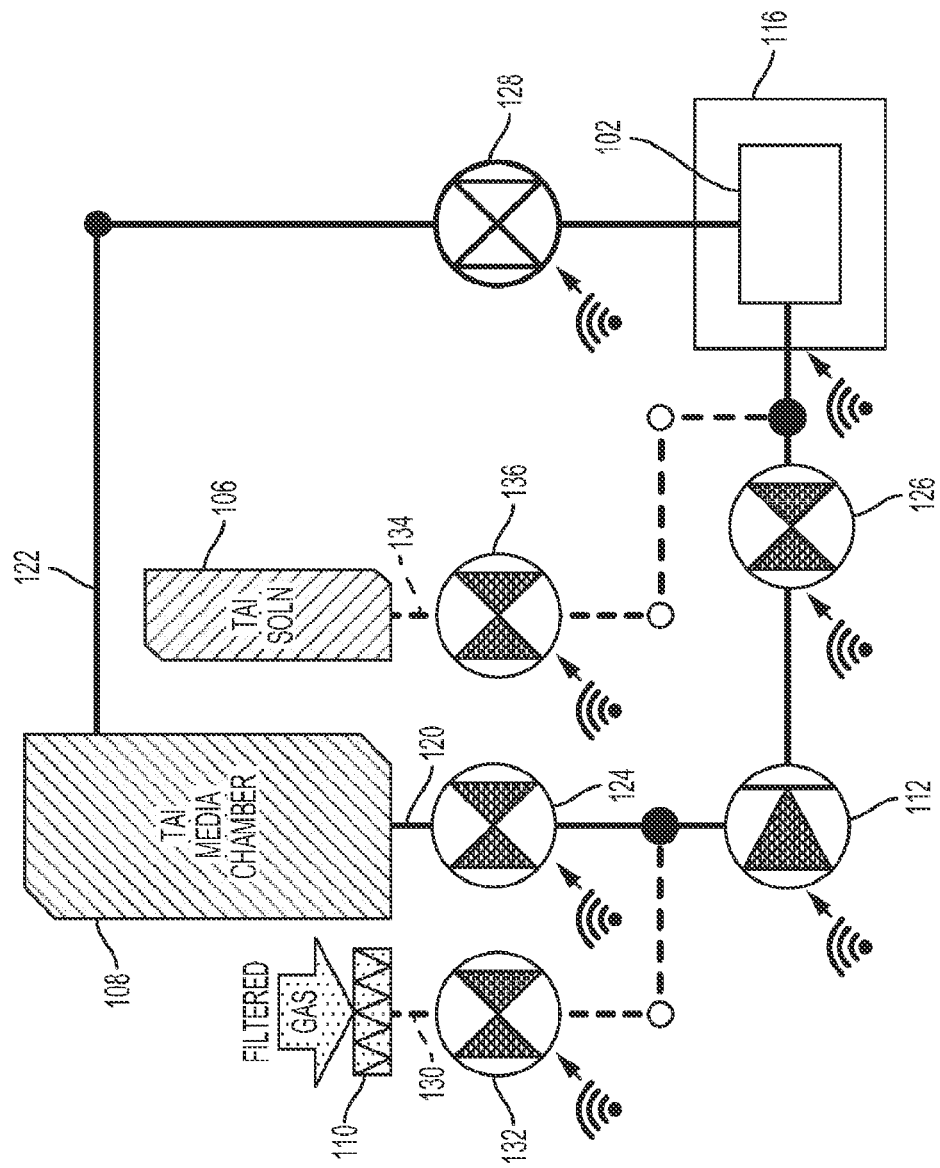
FIG. 16 is a schematic diagram of an alternative circuit configuration of the automated seeding and culturing system according to one embodiment of the present technology.

FIG. 16 is a schematic diagram of an alternative circuit configuration of the system 100. In this configuration, the waste valve 128 may be optional. The removal of the waste valve 128 may limit the performance of the system 100 at the TAI adhesion phase (Phase 6).

In another alternative embodiment, the user may engage in a manual process of rotating the scaffold turner 116 or operating the pump 112. For instance, the user may select such manual operation through the user interface 148. Once the user selects the manual operation, the processor 140 may open the media valve 124, the first chamber valve 126 and the waste valve 128. The processor 140 may instruct the user interface 148 to display a message asking the user for a pump rate. The user may use switches to rotate the scaffold turner 116, or pump TAI media at user defined speeds. The user may pause the process at any time by selecting a pause option at the user interface.

In some embodiments, a surface of a porous scaffold may be treated using liquid and gas pressure to wet and coat the surface of the porous scaffold with a thin layer to facilitate wicking of a cell solution, resulting in a uniform seeded scaffold. The scaffold may be seed and cultured according to methods described earlier.

In some embodiments, the scaffold, the first chamber, the second chamber and the flow circuit may form a preassembled kit for integration into an automated system for scaffold seeding and culturing. The scaffold, the first chamber, the second chamber and the flow circuit may be assembled to form an input to the automated system for scaffold seeding and culturing. The automated system after integration with the preassembled kit may perform seeding TAIs onto the scaffold according to methods described earlier.

Figure 17:
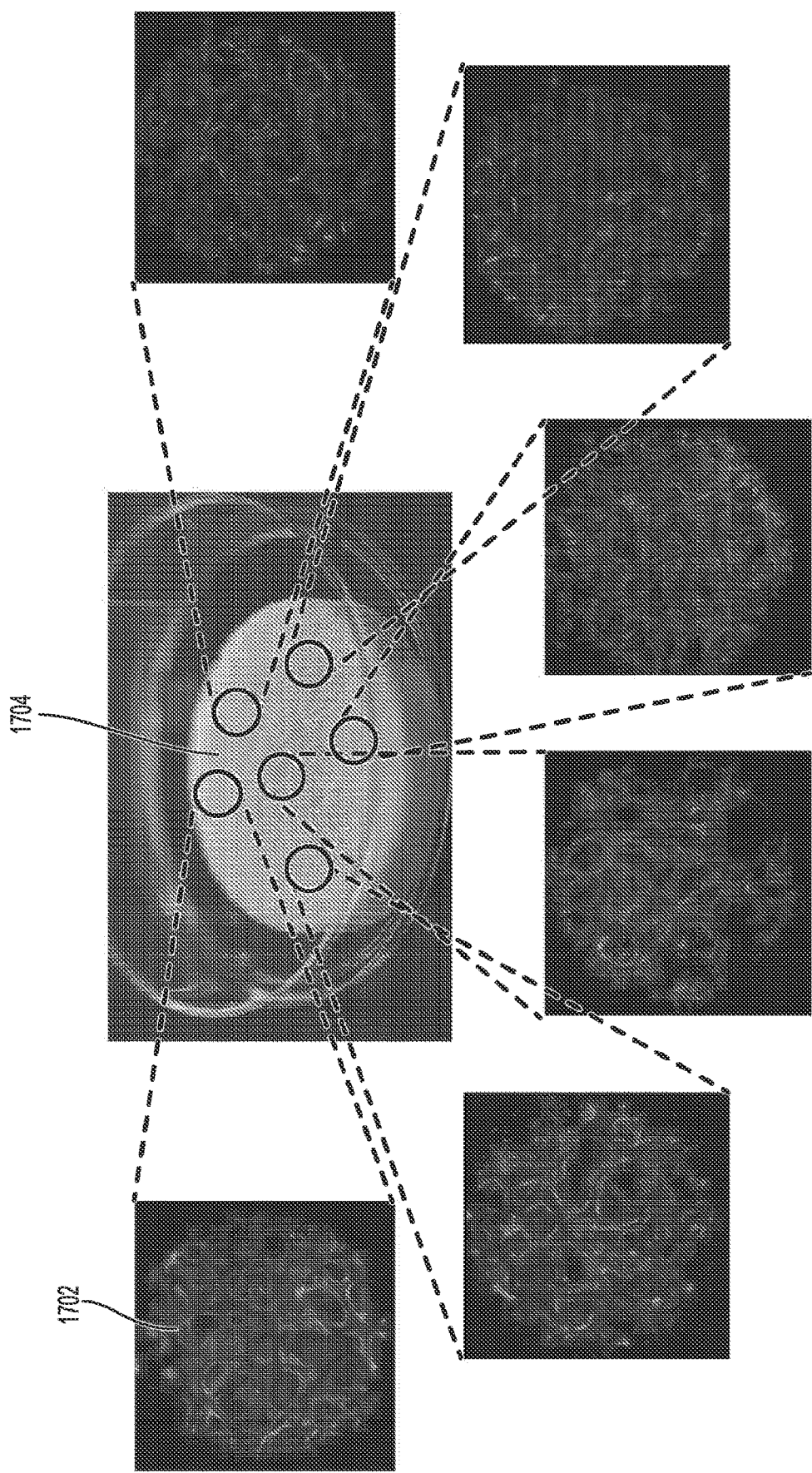
FIG. 17 illustrates homogenous delivery and attachment of ATIs throughout a large porous scaffold.

FIG. 17 illustrates homogenous delivery and attachment of fluorescent labeled ATIs 1702 throughout a large porous scaffold 1704 which for example may have a diameter greater than 5 cm.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some implementations of the disclosed technology.

These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

Implementations of the disclosed technology may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded ono a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special-purpose hardware and computer instructions.

What is claimed is:

1. A system for seeding therapeutic active ingredients (TAIs) onto a porous scaffold, comprising:
    a first chamber for accommodating the porous scaffold;
    a TAI storage device for storing TAIs;
    a second chamber for storing TAI media;
    a gas inlet for receiving gas from a compressed source;
    a flow circuit coupled to (i) the first chamber, (ii) the TAI storage device, (iii) the second chamber and (iv) the gas inlet,
    said flow circuit delivering the TAIs, the TAI media and the gas to the porous scaffold;
    a pump for pumping at least one of the TAIs, the TAI media and the gas in the flow circuit;
    a plurality of valves for regulating a delivery of the TAIs, the TAI media and the gas to the porous scaffold; and
    a processor programmed to regulate seeding and culturing the porous scaffold by switching one or more valves between open and closed positions,
    wherein the plurality of valves include:
        a media valve configured to regulate the delivery of the TAI media from the second chamber to the porous scaffold;
        a gas valve configured to regulate the delivery of the gas from the gas inlet
        a TAI valve for regulating the delivery of the TAIs from the TAI storage device;
        a first chamber valve for regulating the delivery of the gas to the first chamber; and
        a waste valve for regulating a flow from the first chamber, wherein the processor is programmed to perform a pre-wetting process for pre-wetting the porous scaffold with the TAI media, the pre-wetting process comprising the steps of:
(i) setting the media valve, the first chamber valve, and the waste valve to an open position while the gas valve and the TAI valve are in a closed position to pump the TAI media into the first chamber;
(ii) setting the gas valve, the first chamber valve, and the waste valve to an open position while the media valve and the TAI valve are closed to pump the gas into the first chamber; and
(iii) regulating pulsing pressurized gas bursts through the porous scaffold by repeatedly alternating each of the gas valve, the first chamber valve, and the waste valve between an open position and a closed position while the media valve and the TAI valve are in a closed position.

2. The system of claim 1, wherein the flow circuit includes a media supply line and a media return line between the first chamber and the second chamber, a TAI supply line connected to the TAI storage device for delivering the TAIs, and a gas supply line connected to the gas inlet for delivering the gas.

3. The system of claim 1, wherein the processor is configured to adjust a pump speed by the pump.

4. The system of claim 1, wherein the regulation of pulsing pressurized gas bursts includes switching the gas valve to an open position and the first chamber valve to a closed position to generate pressurized gas prior to releasing a pressurized gas burst.

5. The system of claim 4, wherein the processor is configured to switch the gas valve to a closed position and the first chamber valve to an open position to release the pressurized gas burst into the first chamber.

6. The system of claim 1, wherein the processor is configured to regulate releasing the TAIs from the TAI storage device by adjusting the plurality of valves such that the TAI valve and the waste valve are in an open position while remaining valves are in a closed position.

7. The system of claim 6, wherein the processor is configured to regulate pumping the TAIs into the first chamber by adjusting the plurality of valves such that the media valve, the first chamber valve and the waste valve are in an open position while remaining valves are in a closed position.

8. The system of claim 1, further comprising a scaffold turner, driven by a motor, for rotating the porous scaffold accommodated in the first chamber through a plurality of positions.

9. The system of claim 8, wherein the processor is configured to regulate adhesion of TAIs on the porous scaffold by instructing the motor that drives the scaffold turner to rotate the porous scaffold through the plurality of positions.

10. The system of claim 1, further comprising a motor for driving the pump.

11. The system of claim 10, wherein the processor is configured to regulate TAI culturing by instructing the motor that drives the pump to pump the TAI media into the first chamber for a predetermined period of time.

12. The system of claim 1, wherein the compressed source provides $CO_2$, $N_2$ or mixed gases.

13. The system of claim 1, wherein the TAIs further comprise one or a combination of drugs, proteins and hydrogel.

14. A method for seeding and culturing therapeutic active ingredients (TAIs) into a porous scaffold, comprising:
accommodating the porous scaffold in a first chamber;
delivering TAIs, TAI media and gas to the porous scaffold via a flow circuit from a TAI storage device, at least one second chamber and a gas inlet;
pumping at least one of the TAIs, the TAI media and the gas in the flow circuit by a pump; and
regulating a delivery of the TAIs, the TAI media and the gas to the porous scaffold by a processor via a plurality of valves,
wherein the plurality of valves include:
a media valve for regulating the delivery of the TAI media from the second chamber;
a gas valve for regulating the delivery of the gas from the gas inlet
a TAI valve for regulating the delivery of the TAIs from the TAI storage device;
a first chamber valve for regulating the delivery of the gas to the first chamber; and
a waste valve for regulating a flow from the first chamber; and
wherein the processor performs a pre-wetting process for pre-wetting the porous scaffold with the TAI media, comprising steps of:
(i) setting the media valve, the first chamber valve, and the waste valve to an open position while the gas valve and the TAI valve are in a closed position to pump the TAI media into the first chamber;
(ii) setting the gas valve, the first chamber valve, and the waste valve to an open position while the media valve and the TAI valve are closed to pump the gas into the first chamber; and
(iii) regulating pulsing pressurized gas bursts through the porous scaffold by repeatedly alternating each of the gas valve, the first chamber valve and the waste valve between an open position and a closed position while the media valve and the TAI valve are in a closed position.

15. The method of claim 14, wherein the regulation of pulsing pressurized gas bursts includes switching the gas valve to an open position and the first chamber valve to a closed position to generate pressurized gas prior to releasing a pressurized gas burst.

16. The method of claim 15, wherein the regulation of pulsing pressurized gas bursts includes switching the gas valve to a closed position and the first chamber valve to an open position to release the pressurized gas burst into the first chamber.

* * * * *